United States Patent
Song et al.

(10) Patent No.: US 10,822,454 B2
(45) Date of Patent: Nov. 3, 2020

(54) BIODEGRADABLE AMPHIPHILIC SHAPE MEMORY POLYMERS AND COMPOSITIONS AND METHODS THEREOF

(71) Applicant: University of Massachusetts, Boston, MA (US)

(72) Inventors: Jie Song, Shrewsbury, MA (US); Ben Zhang, Worcester, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 16/465,712

(22) PCT Filed: Dec. 3, 2017

(86) PCT No.: PCT/US2017/064384
§ 371 (c)(1),
(2) Date: May 31, 2019

(87) PCT Pub. No.: WO2018/102796
PCT Pub. Date: Jun. 7, 2018

(65) Prior Publication Data
US 2019/0330419 A1  Oct. 31, 2019

Related U.S. Application Data

(60) Provisional application No. 62/429,540, filed on Dec. 2, 2016, provisional application No. 62/449,792, filed on Jan. 24, 2017.

(51) Int. Cl.
*C08G 63/664* (2006.01)
*A61L 27/18* (2006.01)
*A61L 27/58* (2006.01)
*C08K 3/32* (2006.01)

(52) U.S. Cl.
CPC ............ *C08G 63/664* (2013.01); *A61L 27/18* (2013.01); *A61L 27/58* (2013.01); *C08K 3/32* (2013.01)

(58) Field of Classification Search
CPC ......... C08G 63/664; C08G 3/32; A61L 27/18; A61L 27/50
See application file for complete search history.

(56) References Cited

U.S. PATENT DOCUMENTS

| 5,514,380 A | 5/1996 | Song et al. |
| 2007/0156248 A1* | 7/2007 | Marco ................... A61F 5/0036 623/23.7 |
| 2009/0247666 A1 | 10/2009 | Yu et al. |
| 2014/0357806 A1 | 12/2014 | Song et al. |

OTHER PUBLICATIONS

Zhang et al. (Applied Materials and Interfaces 4450-4456).*
Lanao et al. (Tissue Engineering Part B: 19(4) 380-390).*
AKutikov et al. (Macromol. Chem Phys. (2014); 215(24): 2482-2490.*
Li et al. J. Am. Chem. Soc. 2012, 134, 16352-16359.*
Hines et al., Crit Rev Ther Drug Carrier Syst. 2013 ; 30(3): 257-276.*
PolyFacts vol. 9(2) , 2014-2015.*
PCT/US17/64384, Int'l Search Report and Written Opinion of the ISA, dated Feb. 14, 2018.
Wang et al. "New Amphiphilic Poly(2-ethyl-2-oxazoline)Poly(L-lactide) Triblock Copolymers" Biomacromolecules, vol. 4, pp. 1487-1490, Sep. 18, 2003.
Kutikov et al. "Biodegradable PEG-Based Amphiphilic Block Copolymers for Tissue Engineering Applications" ACS Biomaterials Science & Engineering, vol. 1, pp. 463-480, May 26, 2015.
Kin et al. "Injectable and thermosensitive PLGA-g-PEG hydrogels containing hydroxyapatite: preparation, characterization and in vitro release behavior" Biomedical Materials, vol. 7, pp. 1-10, Mar. 29, 2012.
Makadia et al. "PolyLactic-co-Glycolic Acid (PLGA) as Biodegradable Controlled Drug Delivery Carrier" Polymer, vol. 3, pp. 1377-1397, Aug. 26, 2011.

* cited by examiner

*Primary Examiner* — Shirley V Gembeh
(74) *Attorney, Agent, or Firm* — Milstein Zhang & Wu LLC

(57) ABSTRACT

The invention relates to compositions of co-polymers having hydrophilic and biodegradable hydrophobic units or blocks, resulting in improved properties and functionalities suitable for biomedical applications as self-fitting tissue scaffolds or minimally invasive surgical implants.

14 Claims, 16 Drawing Sheets

(a)

$\overline{M}n = 80292;\ \overline{M}w = 123804;\ PDI = 1.54;\ x + y = 95$ $\overline{M}n = 72297;\ \overline{M}w = 111645;\ PDI = 1.54;\ m + n = 259$ (b)

Proliferation & osteogenic diff.
of PDCs on electrospun HA-PELGA

Facile transfer of GFP-BMSC
cell sheets to electrospun HA-PELGA $Rf$: 99.5%; $Rr$: 98.8%     $Rf$: 99.4%; $Rr$: 100% staggered; 0.4 mm line width;
0.8 mm line spacing; Φ = 3 mm

BIODEGRADABLE AMPHIPHILIC SHAPE MEMORY POLYMERS AND COMPOSITIONS AND METHODS THEREOF

PRIORITY CLAIMS AND RELATED APPLICATIONS

This application is the U.S. national phase of and claims priority to PCT/US2017/064384, filed Dec. 3, 2017, which claims the benefit of priority to U.S. Provisional Application Ser. No. 62/429,540, filed on Dec. 2, 2016, and 62/449,792, filed Jan. 24, 2017, the entire content of each of which is incorporated herein by reference.

TECHNICAL FIELDS OF THE INVENTION

The invention generally relates to polymer compositions. More particularly, the invention relates to compositions of co-polymers having hydrophilic and biodegradable hydrophobic units or blocks, resulting in improved properties and functionalities suitable for biomedical applications as self-fitting tissue scaffolds or minimally invasive surgical implants.

BACKGROUND OF THE INVENTION

Significant research effort has been devoted to the development of degradable polymer/bioceramic composite materials for musculoskeletal tissue engineering. Such materials combine the tunable chemical and mechanical properties of synthetic polymers with osteoconductive yet brittle biominerals such as hydroxyapatite (HA), the principle mineral component of bone. HA provides the necessary mechanical strength, enhances the material's osteoconductivity, and serves an important source for calcium and phosphate ions. HA also plays an important role in retaining a variety of proteins on its surfaces as it has been shown to support bone cell attachment and growth factor binding and release, and to expedite healing of bone defects in vivo. (Gaharwar, et al. 2011 *Biomacromolecules* 12, 1641-50; Xu, et al. 20091 *Orthop. Res.* 27, 1306-11; Filion, et al 2011 *Tissue Eng. Part A* 17, 503-11.) Characterized with its high stiffness and brittleness, however, HA alone is not well suited for broad orthopedic applications beyond serving as a non-weight bearing bone void filler.

Allogenic bone grafts, obtained and processed from human donors or animal cadavers, are widely used in the surgical repair of volumetric bone loss as they provide desired osteoconductive structural frameworks without causing donor site morbidity in patient's own skeleton. (Amini, et al. 2012 *Crit. Rev. Bioeng.* 40, 363.) However, the devitalization of periosteum, the thin membrane overlaying long bone surfaces and harboring stem/progenitor cells and signaling molecules critical for injury repair, during allograft processing significantly compromises allograft tissue integration, resulting in long-term failure. (Colnot, et al. 2012 *Orthop. Res.* 30, 1869; Roberts, et al. 2015 *Bone* 70, 10.) A number of strategies have been developed to improve allograft tissue integration, including dip-coating/direct injection of viral vectors expressing BMP-2, RANKL, VEGF and caALK2, angiogenic lipid factor and bone marrow derived stromal cells (BMSCs) onto allograft surfaces. Despite promising enhancement on bone healing, these methods are not always reproducible from a translational perspective. Recently, porcine small intestinal submucosa (SIS) derived scaffolds and synthetic photo-crosslinked hydrogels were used to deliver BMSCs onto the allograft surface with more stable localization, resulting in improved allograft healing. (Zhang, et al. *J* 2005 *Bone Miner. Res.* 20, 2124; Ito, et al 2005 *Nat. Med.* 11, 291; Koefoed, et al 2005 *Mol. Ther.* 12, 212; Rubery 2010 *Spine* 35, 1640; Aronin, et al. 2010 *Biomaterials* 31, 6417; Hernigou, et al. 2014 *Int. Orthop.* 38, 1913; Xie, et al. 2007 *Tissue Eng.* 13, 435; Zhao, et al. 2011 *J. Biomed. Mater. Res. Part B,* 97B, 1; Hoffman, et al. 2013 *Biomaterials* 34, 8887; Hoffman et al. 2015 *Biomaterials* 52, 426.)

These methods, however, have their own limitations. For instance, the SIS-derived scaffolds required multi-step processing and chemical decellularization of animal tissues. On the other hand, in situ irradiation of the hydrogel cocktail applied to the allograft surface and the use of photo initiators present operational inconvenience and perturbation to encapsulated cells.

Electrospun fibrous mesh scaffolds engineered with proper degradation characteristics, cytocompatibility and osteoconductivity are attractive cell supporting matrices for bone tissue engineering. (Khajavi, et al. 2016 *J. Appl. Polym. Sci.* 133.) To better realize their potential for delivering cells to the surface of structural allografts with sustained stability, however, they also need to be engineered for facile and stable wrapping around allografts while retaining adequate mechanical strength in an aqueous environment. Existing electrospun meshes rarely satisfy all these requirements. For instance, too soft of a mesh scaffold could cause unintended damage of both the scaffold and its adherent cells/cell sheets during the surgical manipulation. On the other hand, too stiff of a scaffold will be hard to wrap around and snugly conform to the surface of a structural allograft. In addition, most biodegradable polymers (e.g. polylactides (PLAs)) are hydrophobic in nature. They do not blend well with hydrophilic bone minerals such as hydroxyapatite and tend to weaken upon hydration as a result of the plasticizing effect of water, further complicating their surgical handling. (Neuendorf, et al. 2008 *Acta Biomater.* 4, 1288.)

Shape memory materials can recover from a deformed/strained temporary shape to a "memorized" permanent shape in response to stimuli such as heat, light and magnetic field. In thermal responsive shape memory polymers (SMPs), this is manifested by freezing and activation of polymeric chain motion below and above a transition temperature, respectively. This property is appealing for designing smart materials as minimally invasive surgical implants and self-deployable devices. (Alteheld, et al. 2005 *Angew. Chem.* 44, (8), 1188-1192; Xu, et al. 2010 *Proc. Natl. Acad. Sci. U.S.A* 107, (17), 7652-7657; Julich-Gruner, et al. 2013 *Macromol. Chem. Phys.* 214, (5), 527-536; Lendlein, et al. 2005 *Nature* 434, (7035), 879-882; Wang, et al. 2013 *Angew. Chem.* 52, (42), 11143-11148; Mohr, et al. 2006 *Proc. Natl. Acad. Sci. U.S.A* 103, (10), 3540-3545; Yakacki, et al. 2007 *Biomaterials* 28, (14), 2255-2263; Sharifi, et al. 2013 *Biomaterials* 34, (33), 8105-8113; Lendlein, et al. 2002 *Science* 296, (5573), 1673-1676; Zhang, et al. 2014 *Acta Biomater* 10, (11), 4597-4605; Baker, et al. 2016 *Biomaterials* 76, 388-398.)

Indeed, recent decades have seen great progress in constructing complex architectures and expanding actuation methods of SMPs. (Behl, et al. 2010 *J. Mater. Chem.* 20, (17), 3335-3345; Xie, et al. 2010 *Nature* 464, (7286), 267-270; Huang, et al. 2005 *Appl. Phys. Lett.* 86, (11), 114105; Kumpfer, et al. 20111 *Am. Chem. Soc.* 133, (32), 12866-12874; Fang, et al. 2015 *Nat. Commun.* 6, 7416.) For scaffold-guided tissue engineering, mechanical compliance of a biomaterial scaffold is often required for facile surgical handling/delivery while adequate mechanical strength after implantation in vivo (aqueous environment) is often desired for achieving stable fixation, particularly for weight-bearing applications. Conventional SMPs rarely address the dichotomy of these mechanical characteristics before surgical implantation/during shape programming versus after shape recovery/upon equilibration under physiological conditions. Plasticizing effect of water and the destruction of hydrogen bonding interactions among polymer chains cause most polymers including SMPs to weaken upon hydration. (Jost, et al. 2015 *Eur. Polym. J.* 68, 302-312; Xiao, et al. 2016 *Sci. Rep.* 6, 26393.)

Some amphiphilic polymers containing PEG were recently shown to exhibit unusual hydration-induced stiffening effect. (Xu, et al. 2007 *J. Am. Chem. Soc.* 129, (3), 506-507; Bedoui, et al. 2012 *Soft Matter* 8, (7), 2230-2236.)

A widely used fabrication technology for generating porous thin membrane scaffolds (or fibrous meshes) is electrospinning, where a grounded surface collects a charged polymer jet of nano and/or micro-sized fibers. Previously reported co-electrospinning of various polymers with hydroxyapatite suffers from a variety of limitations, such as material defects, settling of the hydroxyapatite, poor integration and brittleness, low strength and inferior surgical handling properties. Although beneficial effects occur when blending HA with hydrophilic polymers such as poly(hydroxyethyl methacrylate), for example improved toughness, elastic modulus and osteoblast adhesion, unfortunately poly(hydroxyethyl methacrylate) is not biodegradable.

Biodegradable polyesters such as poly(lactic acid) (PLA) are readily electrospinable with established in vitro and in vivo degradation profiles. The intrinsic hydrophobicity of PLA, however, results in its poor mixing and adhesion with hydrophilic HA, making it difficult to achieve adequate structural and mechanical properties in electrospun HA-PLA composite meshes. (Supova 2009 *J. Mater. Sci. Mater. Med.* 20, 1201-13; Qiu, et al. 2005 *Biomacromolecules* 6, 1193-9; Wei, et al. *Macromol. Biosci.* 9, 631-8; Wang, et al 2010 *Appl. Surf Sci.* 256, 6107-6112.) HA-PLA composites often exhibit inferior handling properties (e.g., brittleness) and inconsistent biological performance. Approaches for addressing the lack of interfacial adhesion include the addition of amphiphilic surfactants or modifying HA with surface-grafted polymers to improve interactions with hydrophobic polyesters. (Yang, et al. 2009 *Acta Biomater.* 5, 3295-304; Kim 20071 *Biomed. Mater. Res. A*, 83, 169-77; Qiu, et al. 2005 *Biomacromolecules* 6, 1193-9; Kim, et al. 2006 *J. Biomed. Mater. Res. A* 79, 643-9; D'Angelo, et al 2012 *Biomacromolecules*, DOI 10.1021/bm3000716.)

Thus, there is a critical need for SMPs that are capable of maintaining or strengthening their mechanical properties after shape recovery in an aqueous environment. An un-met need continues to exist for novel synthetic tissue scaffolds with desired structural and biological properties while exhibiting exceptional features such as scalability and ease of use. Achieving such delicate balance requires thoughtful selection and integration of building blocks of the synthetic scaffold, which remains a fundamental challenge in the design of synthetic tissue scaffolds.

SUMMARY OF THE INVENTION

The invention provides novel co-polymers having hydrophilic and biodegradable hydrophobic units or blocks, resulting in improved properties and functionalities suitable for biomedical applications as self-fitting tissue scaffolds or minimally invasive surgical implants.

SMPs and materials disclosed herein maintain adequate or enhanced mechanical properties after shape recovery in an aqueous environment, for example, stable temporary shape fixing and facile shape recovery in warm water accompanied with concomitant enhanced mechanical strengths.

Biodegradable triblock amphiphilic SMPs disclosed herein, e.g., poly(lactide-co-glycolide)-b-poly(ethylene glycol)-b-poly(lactide-co-glycolide) (PELGA), have a poly (ethylene glycol) (PEG) center block and flanking poly (lactic acid) or poly(lactic-co-glycolic acid) blocks. These SMPs offer tunable hydrolytic degradation and favorable integration (e.g., with HA) and the ability to support attachment of bioactive materials (e.g., electrospun HA-PELGA composites supporting the attachment and osteogenesis of periosteum derived cells (PDCs) and the transfer of cell sheets of BMSCs).

Differential scanning calorimetry (DSC), wide-angle X-ray diffraction (WXRD) and small-angle X-ray scattering (SAXS) analyses revealed that the unique stiffening of the amphiphilic SMPs upon hydration was due to hydration-driven microphase separation and PEG crystallization. It is further demonstrated that the chemical composition of degradable blocks in these SMPs may be tailored to affect the persistence of hydration-induced stiffening upon subsequent dehydration. These properties combined open new horizons for these amphiphilic SMPs for smart weight-bearing in vivo applications (e.g., as self-fitting intervertebral discs). This study also provides a new material design strategy to strengthen polymers in aqueous environment in general.

In one aspect, the invention generally relates to an amphiphilic and biodegradable thermoplastic co-polymer of lactic acid, glycolic acid, and ethylene glycol. The co-polymer comprises blocks of poly(ethylene glycol) and blocks of poly(lactic-co-glycolic acid).

In another aspect, the invention generally relates to a composition comprising an amphiphilic and biodegradable co-polymer disclosed herein.

In yet another aspect, the invention generally relates to a composition comprising one or more inorganic minerals; and an amphiphilic and biodegradable co-polymer of lactic acid, glycolic acid, and ethylene glycol.

In yet another aspect, the invention generally relates to an implant or device comprising a composition disclosed herein.

In yet another aspect, the invention generally relates to a biodegradable composite scaffold comprising an amphiphilic and biodegradable co-polymer disclosed herein.

In yet another aspect, the invention generally relates to a biodegradable composite scaffold made from a composition disclosed herein.

In yet another aspect, the invention generally relates to a self-fitting implant or device, comprising an amphiphilic and biodegradable thermoplastic co-polymer comprising blocks of poly(ethylene glycol) and blocks of poly(lactic-co-glycolic acid) forming a 2-D or 3-D scaffold.

In yet another aspect, the invention generally relates to a method for planting an implant or device. The method includes: providing an implant or device of disclosed herein; deforming or straining the implant or device to a temporary shape; planting the implant or device at an organ or tissue location; and causing the implant or device to self-recover to a pre-set or permanent shape fitted to the organ or tissue or a synthetic implant.

DETAILED DESCRIPTION OF THE INVENTION

Figure 1:
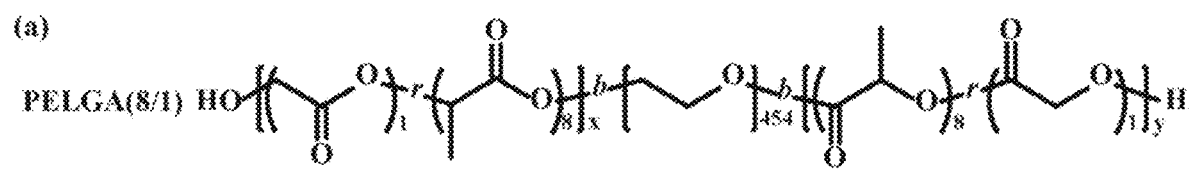
FIG. 1. Electrospun PELGA and HA-PELGA meshes exhibit uniform fiber dimensions, with higher glycolide content accelerating while HA slowing hydrolytic degradation. (a) Chemical structures and compositions of PELGA (8/1) and PELGA(2/1); (b) SEM micrographs of electrospun scaffolds of PELGAs with/without 10 wt % HA; (c) Fiber diameters (n=100, mean±standard deviation) of electrospun scaffolds determined from SEM micrographs using ImageJ. *p<0.05 (student t-tests); (d) In vitro degradation of the electrospun scaffolds (n=3) in PBS (pH 7.4) monitored by mass losses at 37° C. over time.
Figure 1:
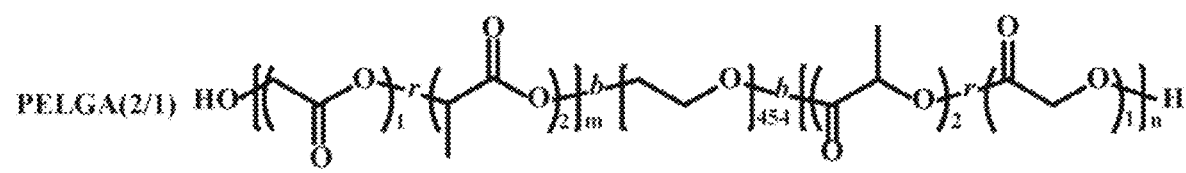
Figure 1:
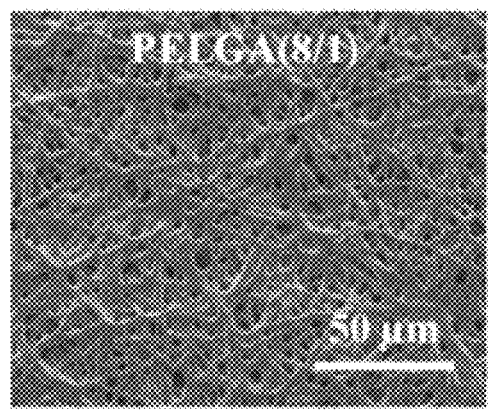
Figure 1:
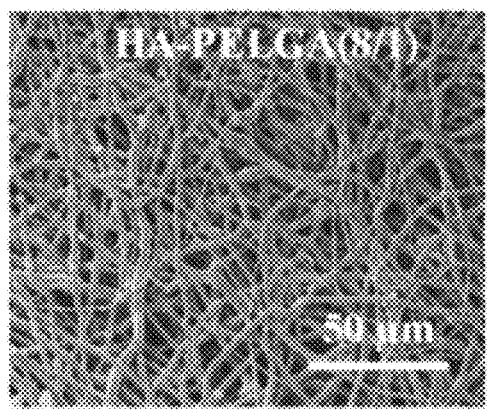
Figure 1:
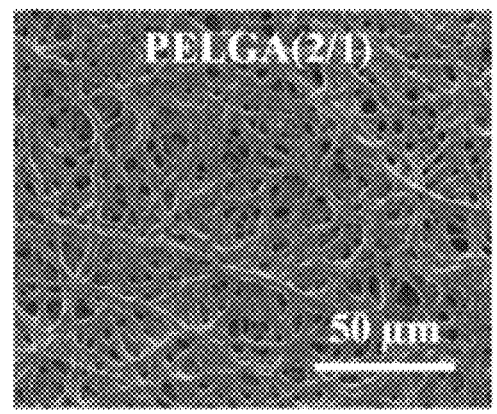
Figure 1:
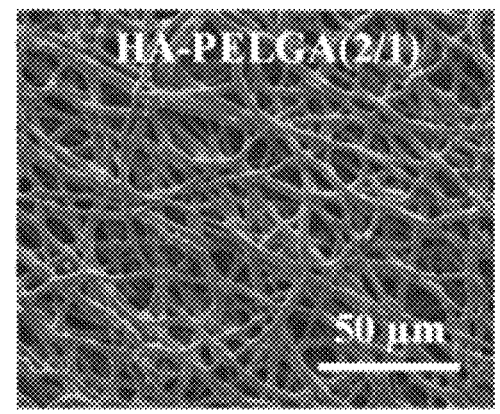
Figure 1:
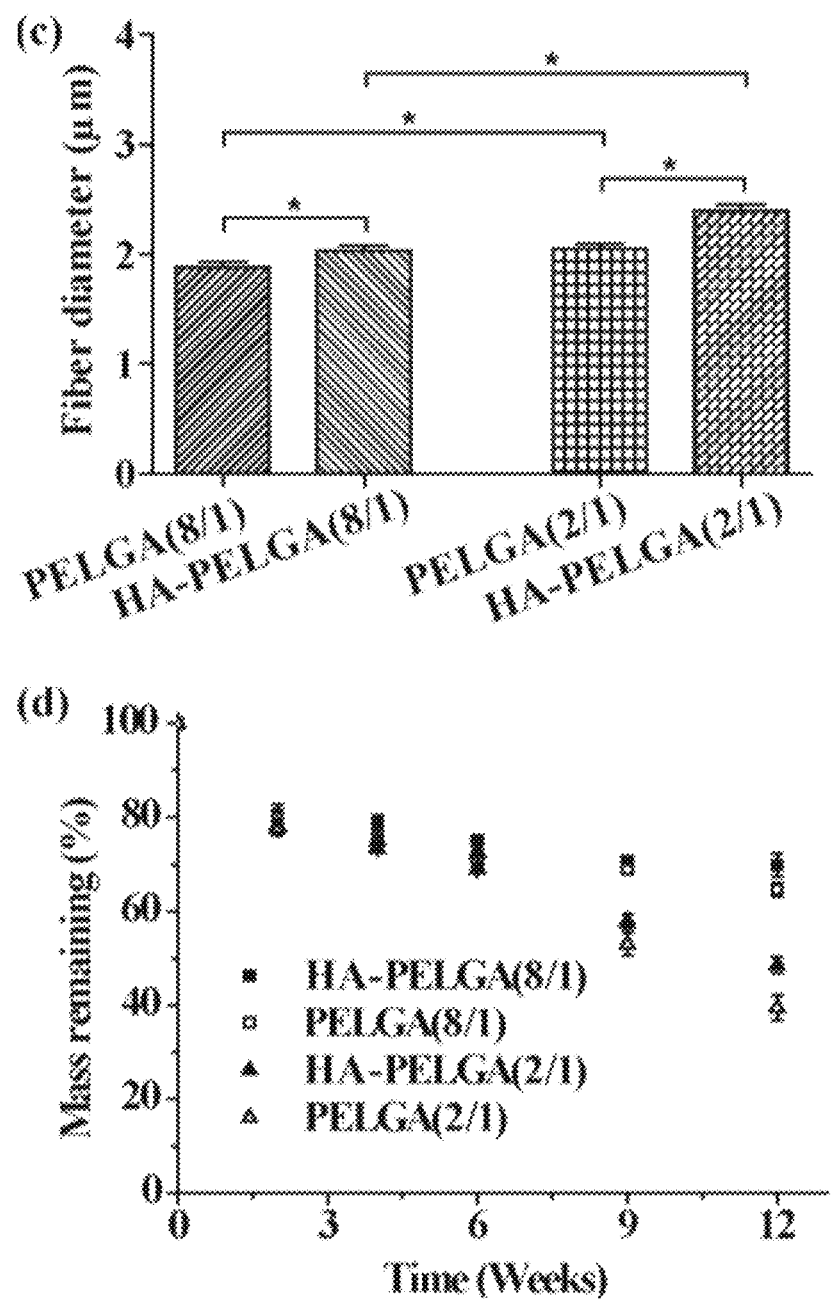

This invention provides novel SMPs and materials that maintain adequate or enhanced mechanical properties after shape recovery in an aqueous environment. The novel co-polymers have hydrophilic and biodegradable hydrophobic units or blocks, resulting in improved properties and functionalities suitable for biomedical applications as self-fitting tissue scaffolds or minimally invasive surgical implants. The desired properties of stable temporary shape fixing and facile shape recovery in warm water are accompanied by concomitant enhanced mechanical strengths.

For example, amphiphilic triblock copolymer poly(lactide-co-glycolide)-b-poly(ethylene glycol)-b-poly(lactide-co-glycolide) (PELGA) was prepared to achieve tunable hydrolytic degradation and favorable integration with HA, and demonstrated the ability of electrospun HA-PELGA composites to support the attachment and osteogenesis of periosteum derived cells (PDCs) and the transfer of cell sheets of BMSCs. It was demonstrated that the amphiphilic composite membranes stiffen upon hydration due to enhanced PEG crystallization, and exhibit desired shape memory behavior around their thermal transitions near physiological temperature. Furthermore, it was demonstrated that these properties combined can indeed translate into efficient self-wrapping of the membrane around bone grafts under physiological conditions to deliver stem cells, thereby establishing HA-PELGA as an exciting synthetic periosteal membrane platform.

In addition, amphiphilic triblock poly(lactic acid)-b-poly(ethylene glycol)-b-poly(lactic acid) (PLA-PEG-PLA, further abbreviated as PELA for ease of data labeling in figures) and poly(lactic-co-glycolic acid)-b-poly(ethylene glycol)-b-poly(lactic-co-glycolic acid) (PLGA-PEG-PLGA, further abbreviated as PELGA for ease of data labeling) were prepared as a class of thermoplastic SMPs capable of self-stiffening upon hydration. Stress-controlled cyclic thermal mechanical testing showed that these SMPs achieved high temporary shape fixing ratio (91-99%) at 4° C. and high shape recovery ratios (96-99%) at 55° C. They also underwent facile shape recovery in warm water with concomitant mechanical strengthening. Using a combination of tensile mechanical testing, DSC, WXRD and SAXS, it was revealed that microphase separation and crystallization differentially contributed to the stiffening effect of these amphiphilic polymer films upon hydration. In addition, it was also demonstrated that the chemical composition of the degradable blocks of the amphiphilic SMPs could be used to tailor the persistence of hydration-induced stiffening upon subsequent dehydration. The safe temperature-triggered efficient shape recovery combined with stiffening of the scaffold upon equilibration in a hydrated envirnoment presents a unique opportunity of the amphiphilic SMPs as smart resorbable orthopedic implants (e.g., for restoring collapsed vertebral disc).

In one aspect, the invention generally relates to an amphiphilic and biodegradable thermoplastic co-polymer of lactic acid, glycolic acid, and ethylene glycol. The co-polymer comprises blocks of poly(ethylene glycol) and blocks of poly(lactic-co-glycolic acid).

The amphiphilic and biodegradable thermoplastic co-polymer of the invention may have any suitable molecular weight, for example, having a molecular weightMW from about 70,000 to about 140,000 (e.g., from about 70,000 to about 140,000, from about 70,000 to about 120,000, from about 70,000 to about 100,000, from about 70,000 to about 90,000, from about 100,000 to about 140,000, from about 120,000 to about 140,000).

The amphiphilic and biodegradable co-polymer of the invention may have any suitable molecular weight of blocks of poly(ethylene glycol), for example, a molecular weight around 20,000 (e.g., about 15,000 to about 25,000, about 18,000 to about 22,000, about 19,000 to about 21,000).

The amphiphilic and biodegradable co-polymer of the invention may have any suitable molecular weight of poly(lactic-co-glycolic acid), for example, ranging from a $M_w$ of about 50,000 to about 120,000 (e.g., from about 50,000 to about 100,000, from about 50,000 to about 100,000, from about 50,000 to about 80,000, from about 60,000 to about 120,000, from about 80,000 to about 120,000, from about 100,000 to about 120,000).

The amphiphilic and biodegradable co-polymer of the invention may have any suitable molar ratio of lactic acid to glycolic acid, for example, from about 19 to about 0.8 (e.g., from about 19 to about 1.0, from about 19 to about 2.0, from about 19 to about 5.0, from about 19 to about 10, from about 15 to about 0.8, from about 10 to about 0.8, from about 5.0 to about 0.8 from about 3.0 to about 0.8 from about 2.0 to about 0.8).

The amphiphilic and biodegradable co-polymer of the invention may have any suitable molar ratio of ethylene glycol to (lactic acid+glycolic acid), for example, from about 0.58 to about 0.79 (e.g., from about 0.58 to about 0.69 from about 0.68 to about 0.79).

In certain embodiments, the amphiphilic and biodegradable co-polymer is characterized by an enhanced mechanical strength upon hydration, for example, with the mechanical strength upon hydration enhanced by microphase separation and/or crystallization.

In another aspect, the invention generally relates to a composition comprising an amphiphilic and biodegradable co-polymer disclosed herein.

In yet another aspect, the invention generally relates to a composition comprising one or more inorganic minerals; and an amphiphilic and biodegradable co-polymer of lactic acid, glycolic acid, and ethylene glycol.

In certain embodiments, the amphiphilic and biodegradable co-polymer comprises blocks of poly(ethylene glycol) and blocks of poly(lactic-co-glycolic acid).

In certain embodiments, the one or more inorganic minerals are selected from the group consisting of calcium apatites, calcium phosphates, hydroxyapatite, and substituted hydroxyapatites.

In certain preferred embodiments, the one or more inorganic minerals is hydroxyapatite.

In certain embodiments, the one or more inorganic minerals are present in a weight percentage up to 60%, (e.g., from about 5% to about 60%, from about 10% to about 60%, from about 20% to about 60%, from about 30% to about 60%, from about 40% to about 60%, from about 5% to about 50%, from about 10% to about 50%, from about 10% to about 40%, from about 10% to about 30%).

In certain embodiments, the composition is characterized by aqueous stability. In certain embodiments, the composition is eletrospinable. In certain embodiments, the composition is thermal extrudable. In certain embodiments, the composition is 3-D printable.

In certain embodiments, the biodegradable amphiphilic block co-polymer is crosslinked forming a three-dimensional polymer-hydroxyapatite network.

In yet another aspect, the invention generally relates to an implant or device comprising a composition disclosed herein.

In yet another aspect, the invention generally relates to a biodegradable composite scaffold comprising an amphiphilic and biodegradable co-polymer disclosed herein.

In yet another aspect, the invention generally relates to a biodegradable composite scaffold made from a composition disclosed herein.

In certain embodiments, the biodegradable composite scaffold is in the form of a 2-D material.

In certain embodiments, the biodegradable composite scaffold is in the form of a 3-D material. In certain embodiments, the biodegradable composite scaffold is in the form of a fibrous mesh or a dense form or 3-D printed macroporous form.

In certain embodiments, the biodegradable composite scaffold of the invention can be used to support attachment, encapsulation, or transfer of cells or cell sheets.

Any suitable cells may be attached, encapsulated or transfered. In certain embodiments, the cells are stem cells or progenitor cells.

In certain embodiments, the biodegradable composite scaffold of the invention can be used to support attachment or encapsulation of a biological agent.

Any suitable biological agents may be attached or encapsulated. In certain embodiments, the biological agent is selected from the group consisting of growth factors, cytokines, gene vectors, antibiotics, anti-inflammatory drugs and bacterial phage.

The biodegradable composite scaffold disclosed herein is suitable and may be used as an implant and/or as a degradable scaffold to guide the regeneration of bone, cartilage, tendon, ligament, osteochondral, or dental bone tissues.

In certain embodiments, the biodegradable composite scaffold is characterized by a shape memory recoverable from a deformed or strained temporary shape to a pre-set or permanent shape in response to stimuli.

Any suitable stimuli may be applied. In certain embodiments, the stimuli comprise contact hydration via contact with water, saline or aqueous media or body fluids.

In certain embodiments, the stimuli comprise heat, light, or magnetic field, or a combination thereof.

Any suitable methods may be sued to fabricate the biodegradable composite scaffold and the implant or device disclosed herein. In certain embodiments, fabrication is by electrospinning. In certain embodiments, fabrication is by thermal extrusion or 3-D printing.

In yet another aspect, the invention generally relates to a self-fitting implant or device, comprising an amphiphilic and biodegradable thermoplastic co-polymer comprising blocks of poly(ethylene glycol) and blocks of poly(lactic-co-glycolic acid) forming a 2-D or 3-D scaffold.

In certain embodiments, the self-fitting implant or device of further includes one or more inorganic minerals attached to or encapsulated in the 2-D or 3-D scaffold.

The self-fitting implant or device may have any desired shape, for example, a mesh, sheet, wire, rod, plate, cylinders, or a shape matching with that of a tissue defect, with and without micro- or macro-pores.

The self-fitting implant or device may have any desired size, for example, having a longest dimension in the range from about 1 mm to about 20 cm (e.g., from about 1 mm to about 15 cm, from about 1 mm to about 10 cm, from about 1 mm to about 5 cm, from about 1 mm to about 1 cm, from about 5 mm to about 20 cm, from about 1 cm to about 20 cm, from about 5 cm to about 20 cm, from about 10 cm to about 20 cm), and/or having a shortest dimension in the range from about 0.2 mm to about 5 cm (e.g., from about 0.2 mm to about 3 cm, from about 0.2 mm to about 1 cm, from about 0.2 mm to about 0.5 cm, from about 0.2 mm to about 1 mm, from about 0.2 mm to about 0.5 mm, from about 0.5 mm to about 5 cm, from about 1 mm to about 5 cm, from about 2 mm to about 5 cm, from about 5 mm to about 5 cm, from about 1 cm to about 5 cm).

In certain embodiments, the self-fitting implant or device further includes a bioactive material, for example, selected from the group consisting of cells, growth factors, cytokines, gene vectors, antibiotics, anti-inflammatory drugs and bacterial phage.

In certain embodiments, the self-fitting implant or device is configured to a deformed or strained temporary shape, which in response to a stimuli, self-recovers to a pre-set or permanent shape fitted to an organ or tissue or a synthetic implant.

Any suitable stimuli may be applied. In certain embodiments, the stimuli comprise contact with water or hydration. In certain embodiments, the stimuli comprise heat, light, or magnetic field, or a combination thereof.

In yet another aspect, the invention generally relates to a method for planting an implant or device. The method includes: providing an implant or device of disclosed herein; deforming or straining the implant or device to a temporary shape; planting the implant or device at an organ or tissue location; and causing the implant or device to self-recover to a pre-set or permanent shape fitted to the organ or tissue or a synthetic implant.

In certain embodiments, causing the implant or device to self-recover comprises a stimuli selected from the group consisting of hydration, heat, light and magnetic field.

The method may be applied any suitable organ or tissue implantation. For example, the organ or tissue may be selected from the group consisting of bone, joint, cartilage, tendon, ligament, osteochondral and dental bone tissues.

EXAMPLES

Figure 5:
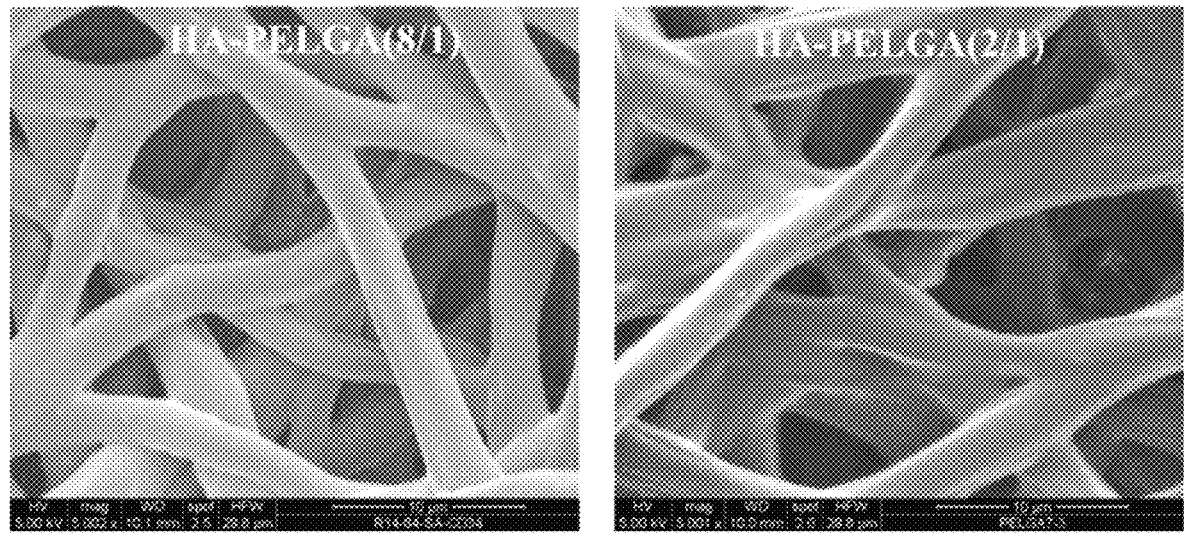
FIG. 5. SEM micrographs of electrospun HA-PELGA(8/1) and HA-PELGA(2/1) showing the composite fibers free of large HA aggregates. Scale bar: 10 μm.

PELGA and HA-PELGA with Varying Glycolide to Lactide Contents were Electrospun with Uniform Fiber Dimensions to Give Meshes with Varying Hydrolytic Degradation Rates PELGA were synthesized by ring opening polymerization of D,L-lactide and glycolide in varying feed ratios using PEG20k as an initiator (FIG. 1a). High molecular weight ($M_w$ 112-124 kD; PDI 1.54) amphiphilic block copolymers PELGA(8/1) and PELGA(2/1) with an incorporated lactic acid (LA) and glycolic acid (GA) unit molar ratio of 8/1 and 2/1 (per $^1$H NMR integration), respectively, were obtained. The high molecular weights enabled PELGAs be readily electrospun into meshes with uniform microfiber dimensions (~2 µm in diameter with tight standard deviation, FIG. 1b). HA is the major mineral component of natural bone and is the most common osteoconductive structural component used in the fabrication of polymer-mineral composite as bone tissue engineering scaffolds. Compared to the pure polymers, HA-PELGA(8/1) and HA-PELGA(2/1) composites were more readily electrospun to give less fused fiber junctions (FIG. 1b) and slightly larger but uniform microfibers diameters (FIG. 1c). (Kim, et al. 2006 *J. Biomed. Mater. Res., Part A,* 79A, 643; Kutikov, et al. 2013 *Acta Biomater.* 9, 8354.) The tight standard deviation of fiber diameters observed with the HA-PELGA composites, along with the smooth fiber morphology free of large mineral aggregates revealed by higher resolution SEM (FIG. 5), supports good dispersion of HA with the amphiphilic polymers. This observation is in stark contrast with the unfavorable mineral aggregations often observed with HA composites formed with hydrophobic polymers. Of note, PELGA (2/1) and HA-PELGA(2/1) meshes exhibited slightly larger fiber diameters than PELGA(8/1) and HA-PELGA(8/1), respectively. (Kim, et al. 2006 *J. Biomed. Mater. Res., Part A*, 79A, 643; Supova, 2009 *J. Mater. Sci.: Mater. Med.* 20, 1201.) The lower solubility of the higher glycolide content PELGA(2/1) in chloroform, consequently higher viscosity of its electrospun solutions, are likely responsible for the relatively compromised electrospinnability.

Timely degradation/resorption of synthetic scaffolds is desired to minimize long-term interference to tissue integration in scaffold-guided tissue regeneration. Incorporation of glycolide can be utilized to tune degradation rates of PLA, with the most expedited degradation achieved at ~1:1/lactic-to-glycolic unit ratio in the resulting PLGA copolymers. (Zhang, et al. 2016 *Rsc Advances* 6, 47418; Makadia, et al. 2011 *Polymers* 3, 1377; Yang, et al. 2004 *Macromolecular Bioscience* 4, 1113.)

Disclosed herein is that after 12-week incubation in PBS (pH 7.4) at 37° C., PELGA(2/1) and PELGA(8/1) lost 60 wt % and 35 wt %, respectively (FIG. 1d), as opposed to <20 wt % weight loss without any GA incorporation. Incorporation of HA, a weak base that can buffer the acidic degradation product of PLGA and autocatalytic effect of PLA degradation, slowed down the degradation of PELGA scaffolds, resulting in 49 and 70 wt % mass residues of HA-PELGA (2/1) and HA-PELGA(8/1) scaffolds after 12-week incubation in PBS, respectively. (Huang, et al. *J. Nanomater.* 2013.)

Hydration Stiffened Amphiphilic PELGA and HA-PELGA Due to Enhanced PEG Crystallization Polymeric material's mechanical properties depend not only on their chemical composition but also their phase structures. The as-spun HA-PELGA scaffolds were soft and non-free standing (FIG. 2a, left), with the higher GA-content HA-PELGA(2/1) composite softer than HA-PELGA (8/1) (FIG. 2b). The polymer chains of PELGA(8/1) may be more stretched and aligned during electrospinning due to better solubility in chloroform, thereby facilitating crystallization of PEG segments. Both composites significantly stiffened after hydration in deionized (DI) water for 24 h at room temperature (r.t.) followed by lyophilization (FIG. 2a, right), with the tensile modulus of as-spun HA-PELGA(2/1) increasing from 58 to 206 MPa while that of HA-PELGA (8/1) increasing from 175 to 330 MPa (FIG. 2b).

Literature on hydration-facilitated crystallization and enhancement of stiffness of amphiphilic triblock polymers containing PEG has been very limited and such a phenomenon is quite surprising as PEG is considered as water soluble segments. (Kutikov, et al. 2013 *Acta Biomater.* 9, 8354; Kutikov, et al. 2015 *ACS Biomater. Sci. Eng.* 1, 463.) To elucidate polymer phase structures of electrospun PELGA and HA-PELGA as well as their changes underlying the hydration-induced stiffening effect, DSC and X-ray powder diffraction (XRD) were carried out. DSC scans showed that the as-spun PELGA(2/1) scaffold underwent an endothermic process around 56° C., with a transition enthalpy of 3.5 J/g (FIG. 2c). This thermal transition approximates the melt of PEG crystals (FIG. 2c, bottom), supporting that some PEG segments in PELGA(2/1) have likely crystallized during electrospinning. Comparing to the higher melting enthalpy of 184 J/g for PEG20k, the lower enthalpy observed with PELGA(2/1) could be attributed to the imperfect/incomplete crystallization of PEG segments in a confined environment. XRD confirmed the crystallization of PEG segments of as-spun PELGA(2/1) wherein two peaks at 4.6 and 3.8 Å characteristic of the diffractions of pure PEG20k were observed (FIG. 2d). Consistent with hydration-induced stiffening, PELGA(2/1) exhibited a higher melting enthalpy of 8.4 J/g attributable to enhanced PEG crystallization after hydration (FIG. 2c). Interestingly, the incorporation of HA with PELGA(2/1) suppressed the PEG domain crystallization during electrospinning as shown by the lack of PEG melting peaks in DSC curve (FIG. 2c) and characteristic crystalline PEG XRD diffraction peaks (FIG. 2d) of as-spun HA-PELGA(2/1). This observation supports that the interaction between HA and PEG segments disrupts the relatively weak PEG crystallization in the higher GA-content amphiphilic composite, consistent with the weaker mechanical strength of HA-PELGA(2/1) compared to HA-PELGA(8/1) (FIG. 2b). Hydration, however, promoted the PEG crystallization in HA-PELGA(2/1) composite as supported by DSC and XRD (FIGS. 2c and 2d), consistent with its enhanced tensile modulus upon hydration (FIG. 2b).

PELGA(8/1) and HA-PELGA(8/1) showed similar trend of enhancement in PEG crystallization upon hydration as PELGA(2/1) and HA-PELGA(2/1) (FIGS. 2c and 2d). The effect of HA incorporation on PEG crystallization of PELGA(8/1) was less pronounced, only resulting in a decrease in PEG melt enthalpy from 10.1 to 6.9 J/g. This observation is consistent with better stretching/alignment of PELGA(8/1) than PELGA(2/1) during electrospinning that may favor PEG crystallization even in the presence of the competing interaction of HA with the hydrophilic PEG domains.

Figure 3:
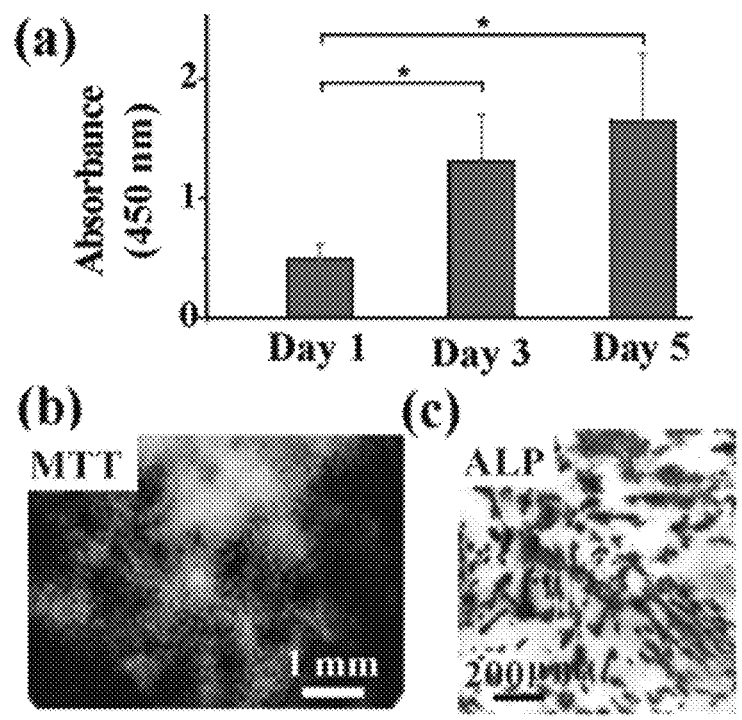
FIG. 3. Electrospun HA-PELGA(2/1) readily support the proliferation and osteogenic differentiation of PDCs as well as the facile transfer of BMSC cell sheets. (a) Cell viability of rat PDCs (n=5; initial seeding density: $1\times10^5$ cells/cm$^2$) adhered on the scaffold and cultured in expansion media as determined by CCK8 over time. *p<0.05 (Student t-test); (b) MTT staining of a PDC-laden membrane on day 5; (c) Alkaline phosphatase (ALP) staining of a PDC-laden membrane on day 11 of osteogenesis culture (initial seeding density: $2.5\times10^5$ cells/cm$^2$); (d) Fluorescent (FL) and bright field (BF) images electrospun HA-PELGA(2/1) with (top) and without (bottom) transferred GFP-labelled BMSC cell sheets. GFP-BMSCs were cultured to confluency on temperature sensitive UpCell™ culture dish and chilled to 4° C. for 30 s to allow cell sheet release and transfer to the electrospun membrane.
Figure 3:
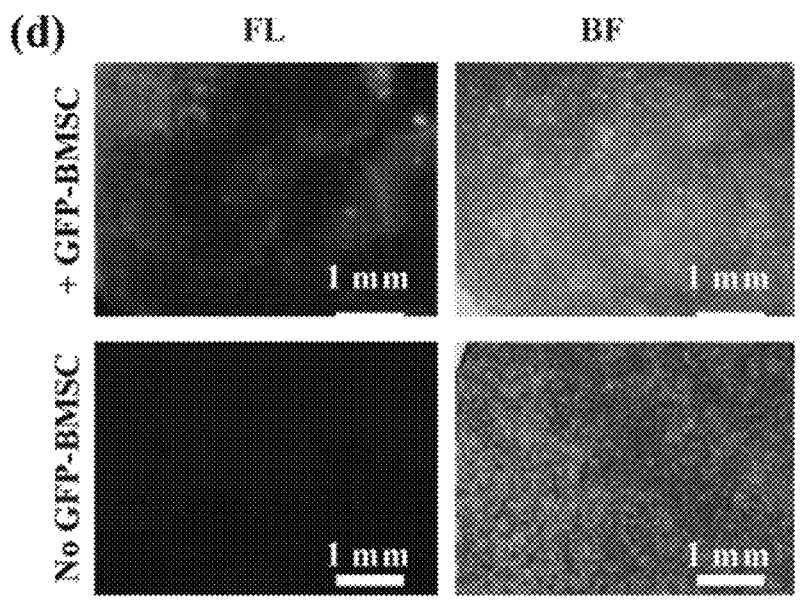

Electrospun HA-PELGA Readily Supported Attachment, Proliferation and Osteogenic Differentiation of Skeletal Progenitor Cells and the Facile Transfer of Stem Cell Sheet The osteoconductive HA-PELGA composite meshes readily supported the attachment and proliferation of PDCs and BMSCs, two skeletal progenitor cells commonly involved in fracture healing and traumatic long bone injury repair. As shown with the faster-degrading HA-PELGA(2/1), PDCs rapidly adhered to the osteoconductive composite mesh within an hour of cell seeding, and readily proliferated as supported by CCK-8 cell viability assay over time (FIG. 3a). MTT staining of the cells adhered on the mesh on day 5 confirmed cell viability and the general cytocompatibility of the composite mesh (FIG. 3b). When cultured in osteogenic media, the adhered PDCs underwent robust osteogenic differentiation as evidenced by positive alkaline phosphatase (ALP) staining detected on the cell-laden mesh on day 11 (FIG. 3c).

BMSCs were also able to attach and undergo osteogenic differentiation on these electrospun membranes, although the cell attachment was generally slower and less efficient than PDCs. Whereas applying centrifugation following initial cell seeding could improve BMSC seeding efficiency on the scaffold, the feasibility was explored of transferring stem cell sheets formed on temperature-sensitive culture surfaces to the membrane as an alternative. Cell sheets retaining intact cell-cell junctions and deposited extracellular matrix (ECM) are attractive for constructing complex tissue architectures, and may be readily released from culture surfaces covalently tethered with poly(N-isopropylacrylamide) when temperature was lowered from 37° C. to 20° C. or below while the surface polymers undergo hydrophobic-to-hydrophilic transition. (Yamato, et al. 2004 *Mater. Today* 7, 42.)

Green-fluorescent protein-labelled rat BMSCs (GFP-BMSCs, transfected as reported) was cultured to confluency on Nunc UpCell™ culture dish (Thermo Scientific) before removing culture media and placing an HA-PELGA(2/1) electrospun membrane over the cell layer at 4° C. for 30 s. (Kutikov, et al. 2015 *ACS Applied Materials & Interfaces* 7, 4890.) Fluorescent microscopy confirmed that the GFP-labelled cell sheet detached from the temperature-responsive culture surface was successfully transferred and attached to the osteoconductive membrane surface (FIG. 3*d*).

Figure 2:
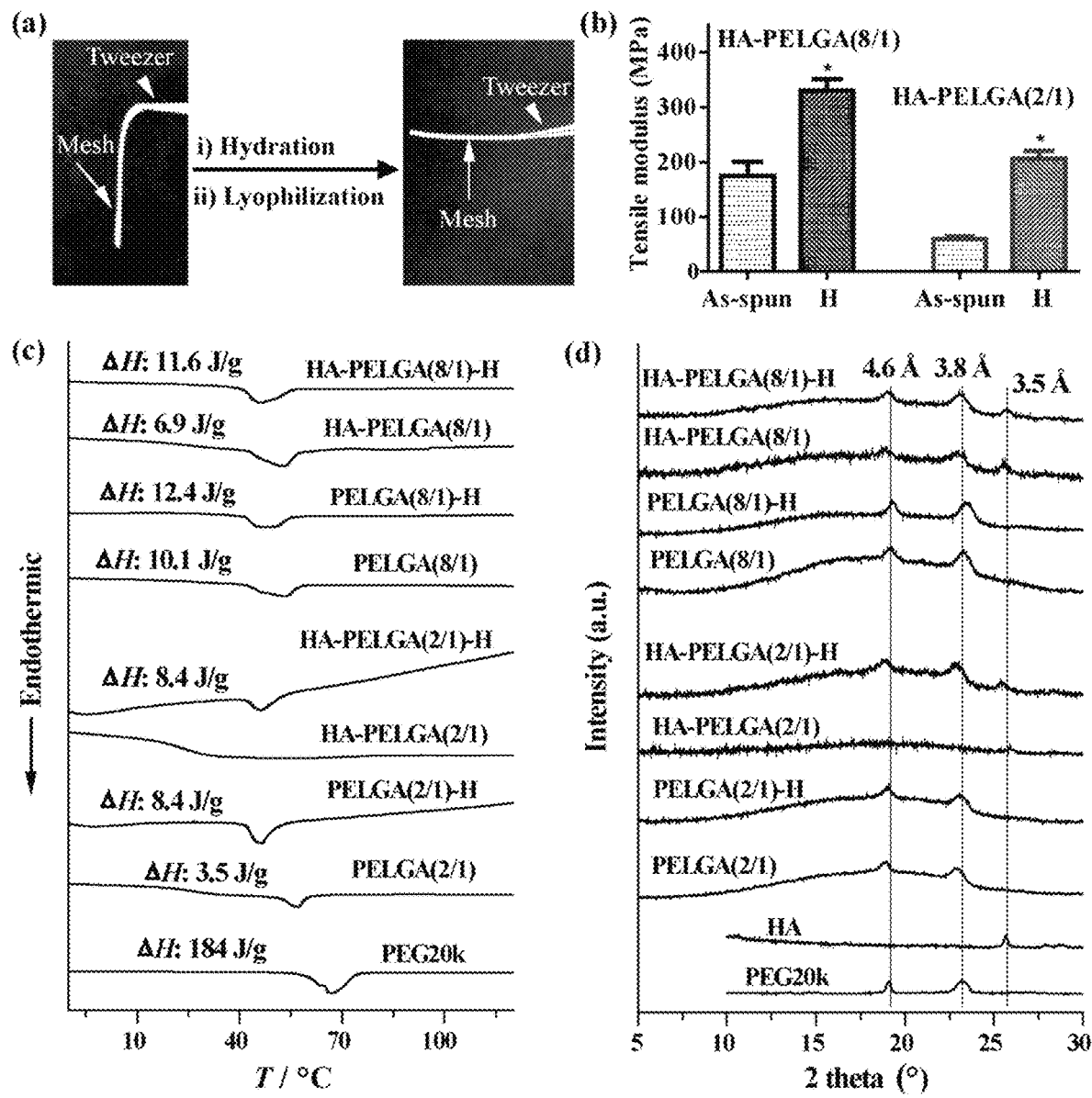
FIG. 2. Hydration stiffens electrospun PELGA and HA-PELGA meshes due to enhanced PEG crystallization. (a) Images of a tweezer holding an electrospun HA-PELGA(2/1) mesh before and after 24-h hydration in DI water followed by lyophilization; (b) Tensile moduli of as-spun or hydrated and subsequently lyophilized (H) HA-PELGA(8/1) and HA-PELGA(2/1) scaffolds (n=5); *p<0.05 (Student t-tests). (c) DSC and (d) XRD of as-spun or hydrated and subsequently lyophilized (H) scaffolds of PELGA (8/1) and PELGA (2/1) with or without 10 wt % HA, along with PEG20k or HA control. H: lyophilized scaffolds after 24-h hydration in DI water at r.t.
Figure 4:
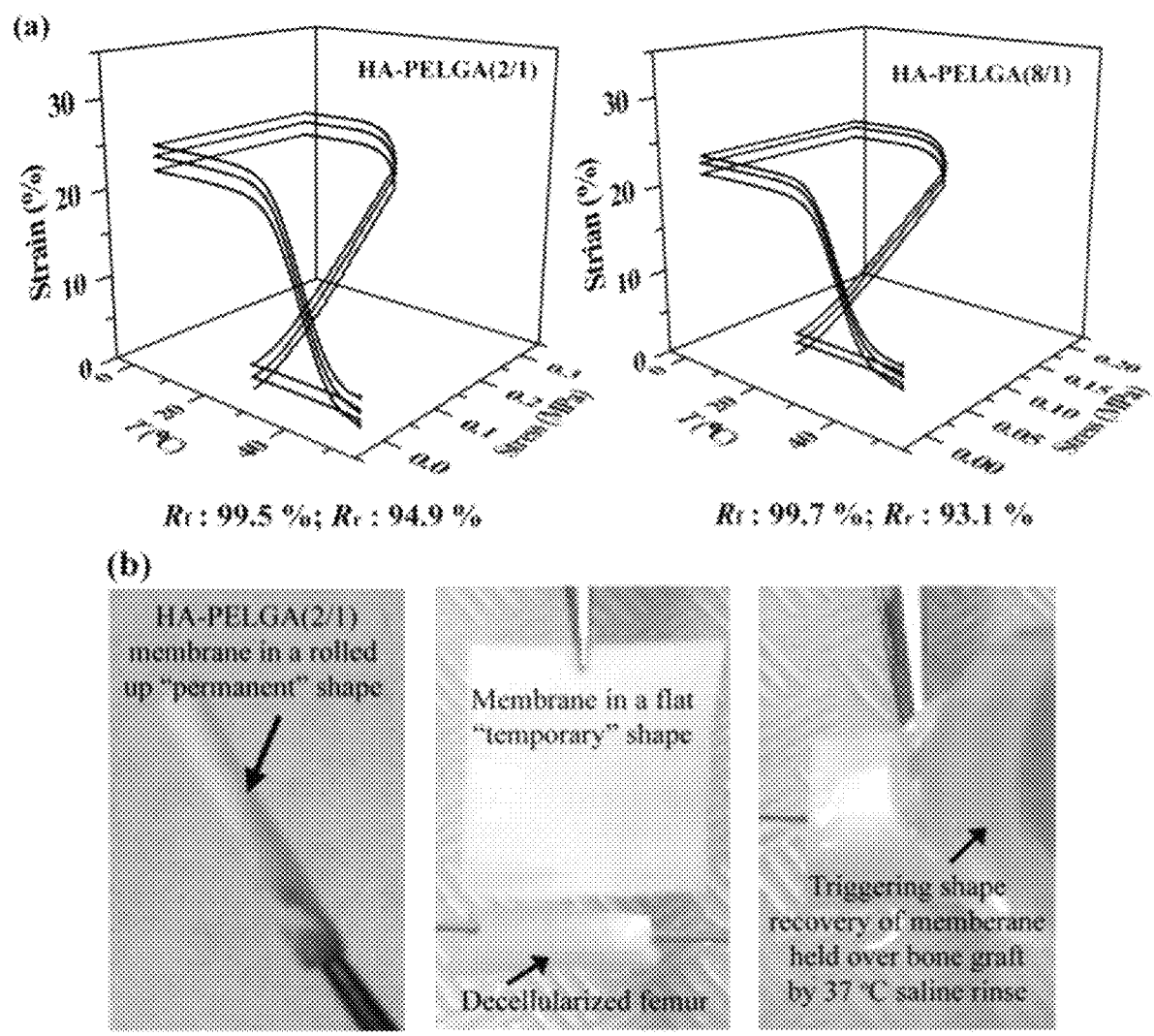
FIG. 4. Temperature-sensitive shape memory behavior of electrospun HA-PELGA and facile self-wrapping of the osteoconductive membrane around femoral bone grafts triggered by 37° C. saline rinse. (a) Stress-controlled thermal mechanical test of electrospun HA-PELGA(8/1) and HA-PELGA(2/1) membranes. The first three cycles for each specimen were shown in the plots; $R_f$ and $R_r$ were calculated based on the second cycle. (b) Permanent shape programming, temporary shape fixing and permanent shape recovery of HA-PELGA(2/1) membrane for self-wrapping around a devitalized rat femoral bone graft. (c) A GFP-BMSC-laden HA-PELGA(2/1) membrane self-wrapped around a devitalized rat femoral bone graft following the shape recovery process (top) and the fluorescent micrograph revealing GFP-BMSCs adhered on the unwrapped membrane (bottom).
Figure 4:
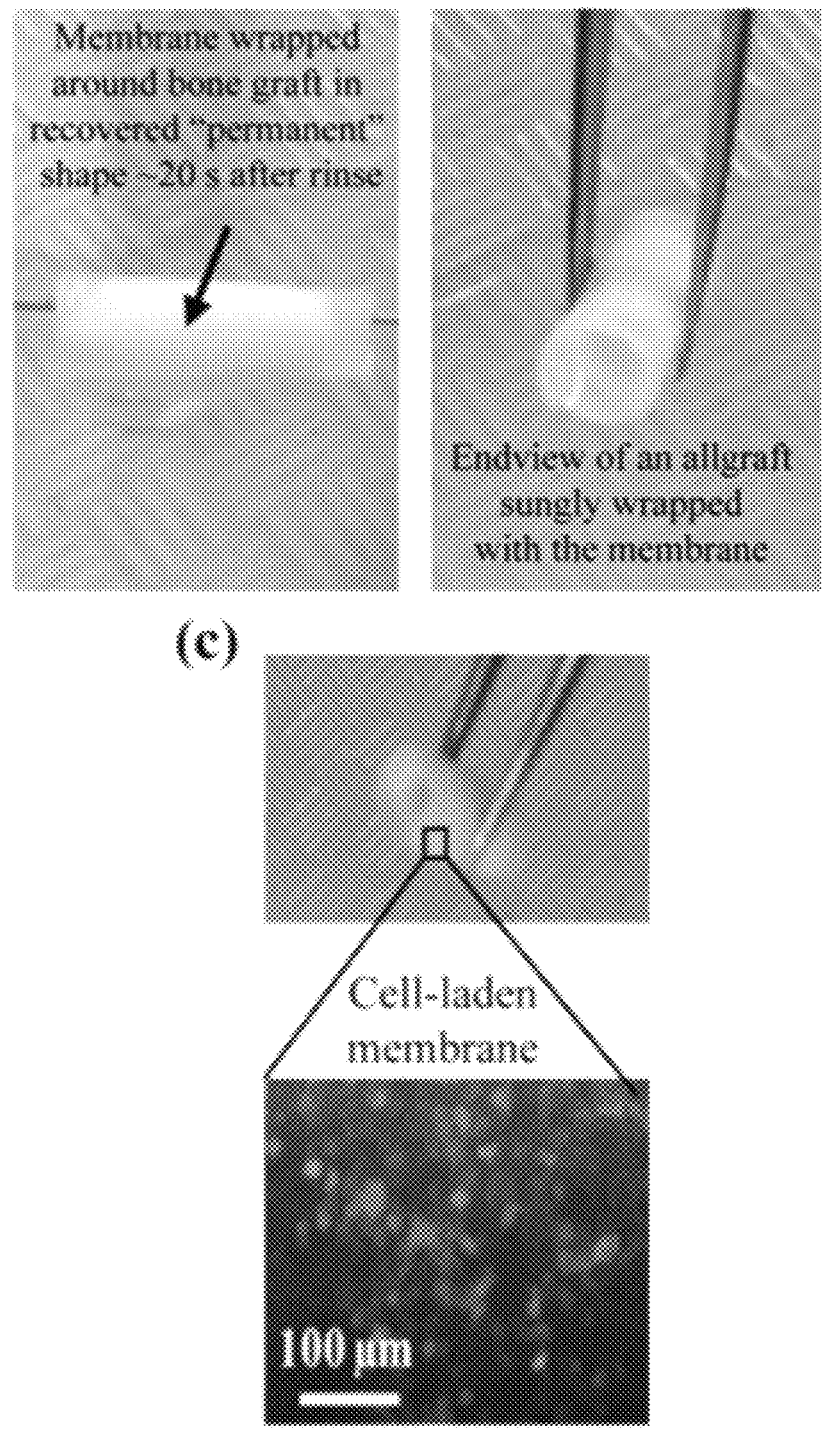
Figure 6:
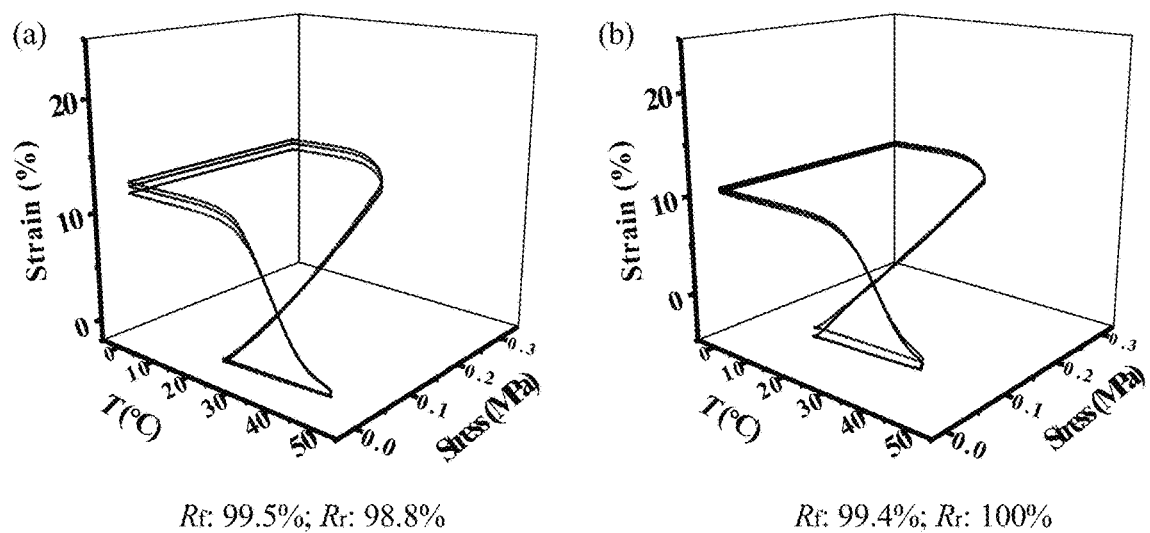
FIG. 6. Stress-controlled cyclic thermal mechanical test of electrospun PELGA(2/1) (a) and PELGA(8/1) (b) membranes. The first three cycles for each specimen were shown in the plot; $R_f$ and $R_r$ were calculated based on the second cycle.

Temperature-Sensitive Shape Memory Behavior of Electrospun HA-PELGA Enabled Facile Cell Delivery Through Self-Wrapping of Cell-Laden Osteoconductive Membranes Around Femoral Bone Grafts at Body Temperature Amphiphilic thermoplastic polymers with sufficient molecular weights and appropriate block compositions could be designed to exhibit distinct thermal transitions around physiologically relevant temperatures. (Kutikov, et al. 2014 *Macromol. Chem. Phys.* 215, 2482.) Stress-controlled cyclic thermal mechanical testing was conducted to quantify shape-memory properties of HA-PELGA composite membranes, which were stretched at 25° C., cooled to 0° C. to fix the temporary shape, and subsequently allowed to undergo shape recovery at 50° C. Both HA-PELGA(8/1) and HA-PELGA(2/1) exhibited excellent fixing ratio of >99% and high shape recovery ratio of 94.9% and 93.1%, respectively (FIGS. 4*a* and 4*b*). Whereas the >99% shape fixing ratios of HA-PELGAs were consistent with those exhibited by the electrospun meshes without HA, the shape recovery ratios were slightly lower than those of PELGA(8/1) ($R_r$: 100%) and PELGA(2/1) ($R_r$: 98.8%) (FIG. 6). Under the same tensile stress applied (0.3 MPa), electrospun HA-PELGAs were stained more (more compliant) than the respective PELGAs, consistent with the reduced PEG crystallization (reduced stiffness) upon incorporation of HA shown by DSC and XRD (FIG. 2).

To demonstrate potential translation of the shape memory behavior of HA-PELGA membranes for safe and efficient self-wrapping around structural bone grafts, HA-PELGA(2/1) was programed into a rolled up "permanent" shape by wrapping it around a tweezer held in 37° C. water bath for 10-30 min (FIG. 4*b*). The membrane was then unrolled into a flat "temporary" shape (a configuration desired for stem cell sheet transfer) at r.t. and fixed at 4° C. When held over a devitalized rat femoral bone graft and rinsed by 37° C. saline, the flat membrane immediately underwent shape recovery into the rolled up "permanent" shape (~20 sec of the rinse) to snugly wrap around the bone graft (FIG. 4*b*). Such a facile shape recovery process triggered by safe saline rinse at body temperature (demonstrated by both HA-PELGA(2/1) and HA-PELGA(8/1) membranes), coupled with the stiffness enhancement of the membrane upon equilibrating in aqueous in vivo environment, promises to significantly improve the surgical handling and stable fixation of the mesh around structural allografts. It was also confirmed the self-wrapping process using GFP-BMSC seeded membranes (FIG. 4*c*). These attractive smart delivery and surgical fixation characteristics, along with the ability to support stem/progenitor cell attachment and osteogenesis, make HA-PELGA promising self-wrapping synthetic periosteal membranes to augment allograft healing for long bone injury repair.

Triblock amphiphilic PELGAs with varying lactide/glycolide contents were readily mixed with HA and electrospun into microfibrous membranes. The hydrolytic degradation of the membranes was found to be expedited with increasing glycolide-to-lactide ratio (PELGA(2/1)>PELGA(8/1) >PELA) while slowed by HA incorporation due to its ability to buffer acidic degradation products. These polymers and their HA composites exhibited hydration induced stiffening as a result of enhanced crystallization of PEG segments as revealed by DSC and XRD. The amphiphilic composites also exhibited thermal responsive shape memory properties around safe physiological temperatures, enabling permanent shape programing in warm water, facile deformation into temporary shape at r.t. and fixation at 4° C., and efficient shape recovery triggered by saline rinse at body temperature. These unique features of HA-PELGA scaffolds make it possible to achieve smart self-wrapping (shape memory property) and sustained stable fixation around bone graft (stiffening upon equilibration in aqueous environment) that is hard to accomplish with conventional polymer meshes. These osteoconductive meshes also readily supported the attachment, proliferation and osteogenic differentiation of skeletal progenitors PDCs as well as the transfer of cell sheets of BMSCs. Collectively, these findings establish shape memory HA-PELGA as an exciting platform for enabling facile cell delivery and engineering synthetic periosteal microenvironment to enhance bone allograft healing and skeletal tissue regeneration outcomes.

Figure 7:
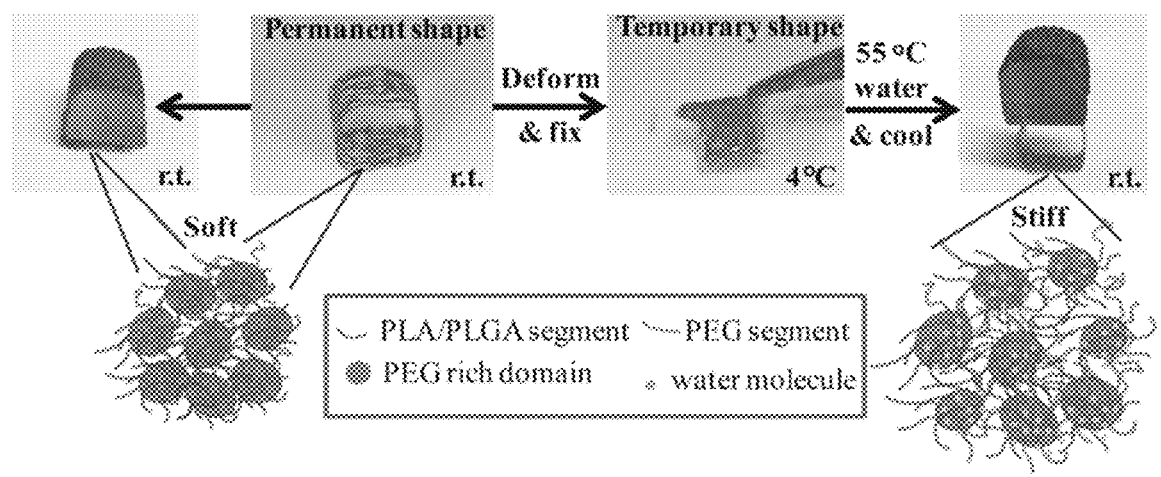
FIG. 7. Thermal responsive shape memory properties of PELA and PELGA films and their facile shape recovery and stiffening in warm water. (a) Chemical structures and compositions of PELA and PELGA. x+y=402, n+m=64. (b) Stress-controlled cyclic thermal mechanical testing of dry PELA and PELGA films. $R_f$ and $R_r$ are calculated from the second cycle. (c) Facile Shape recovery of PELA in 55° C. water with concomitant mechanical strengthening. (d) Facile Shape recovery of PELGA in 55° C. water with concomitant mechanical strengthening. Films were marked by red sharpie for easy visualization.
Figure 7:
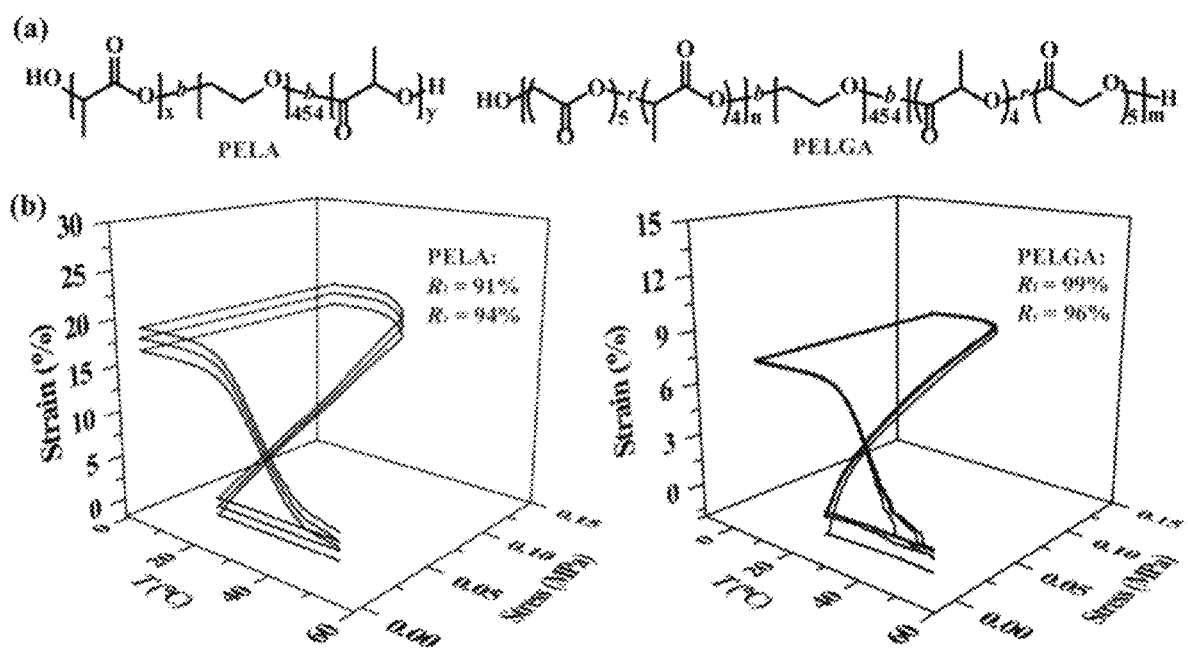
Figure 7:
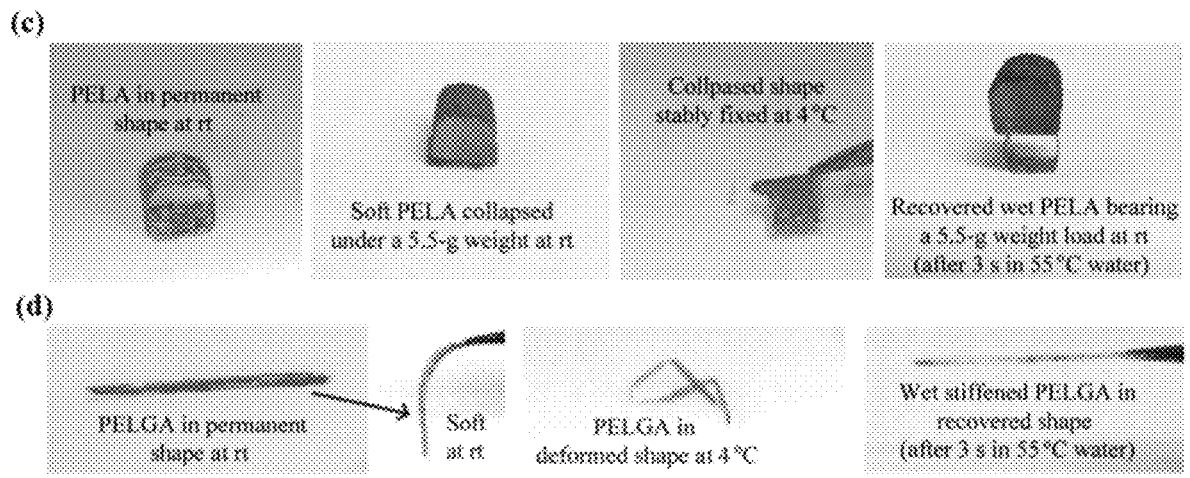
Figure 12:
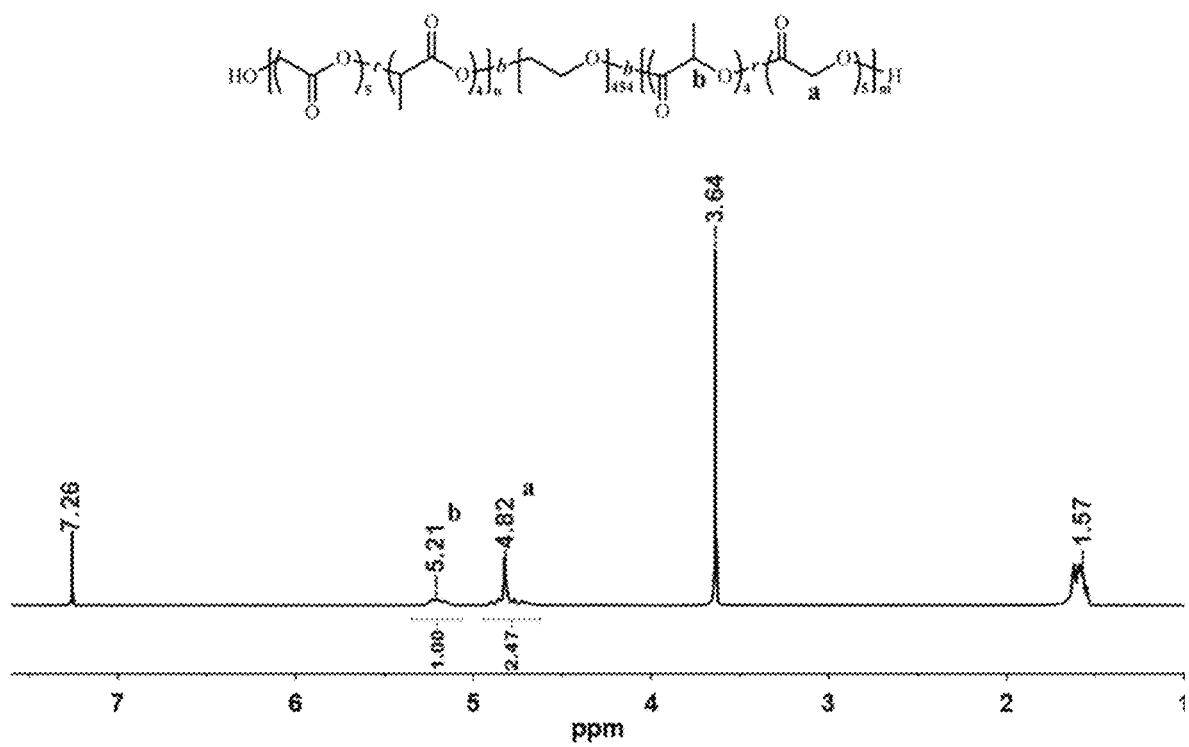
FIG. 12. $^1$H NMR spectrum of PELGA in CDCl$_3$. The actual incorporation content of lactide to glycolide was 4:5 based on the integration of proton signals at 5.21 ppm vs. 4.82 ppm.

Thermal Responsive Shape Memory Properties of PELA and PELGA and Warm Water Induced Shape Recovery with Concomitant Stiffening Triblock amphiphilic polymers PELA ($M_w$=80119, PDI=1.7) and PELGA ($M_w$=94761, PDI=1.7; FIG. 7*a*) consisting a hydrophilic PEG ($M_n$=20 kD) center block and two flanking hydrophobic poly(D,L-lactic acid) (PLA) blocks or hydrophobic random copolymers of D,L-lactide and glycolide (PLGA) at 4:5 ratio were synthesized by ring opening polymerization (FIG. 12). Solvent-cast PELA and PELGA films (residue solvent chloroform was removed under vacuum and validated by NMR) exhibited excellent shape memory properties within a physiologically safe temperature range. Stress-controlled cyclic thermal mechanical tests of dry specimens revealed high fixation ratios ($R_f$) of 91% and 99% at 4° C. as well as high recovery ratios ($R_r$) of 94% and 96% upon equilibration at 55° C. for 5 min for PELA and PELGA films, respectively (FIG. 7*b*). Interestingly, when warm water was used to trigger the shape recovery, it was found that their efficient shape recovery was also accompanied with concomitant stiffening. As demonstrated in FIG. 7*c*, a PELA thin film rolled into a permanent open ring shape was soft at rt and would collapse under a 5.5-g weight load. Upon fixing the collapsed PELA at 4° C. and then immersing in 55° C. water, it rapidly (<3 s) reverted to its permanent shape while significantly stiffened to readily withstand the 5.5-g weight load. Similarly, it was also demonstrated equally efficient shape recovery and stiffening of PELGA in warm water (FIG. 7*d*).

Figure 8:
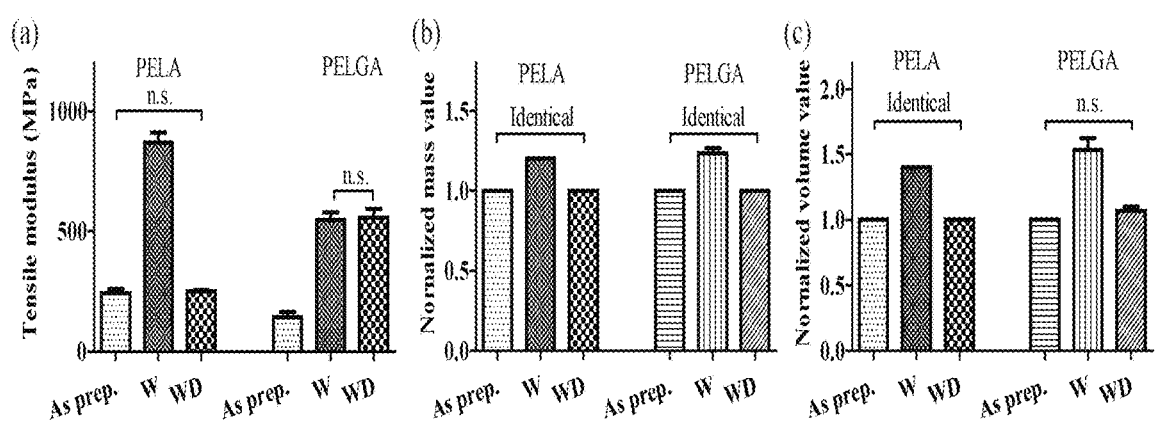
FIG. 8. Room temperature (rt) hydration stiffened and swelled PELA and PELGA films while subsequent dehydration softened PELA but not PELGA. (a) Tensile moduli, (b) relative masses and (c) relative volumes of as prepared (As prep.) cast films, wet films after 24-h hydration in DI water (W), and lyophilized cast films following 24-h hydration (WD) of PELA and PELGA. Specimen dimension for tensile modulus test: 5 mm×40 mm×~0.15 mm (n=5). Specimen for relative masses and volume changes test: discs with a diameter of 6 mm and thickness ~0.15 mm (n=3). All pair-wise comparisons show statistically significant differences (p<0.05; student's t-test) unless denoted as "Identical" or n.s. (not significant).
Figure 13:
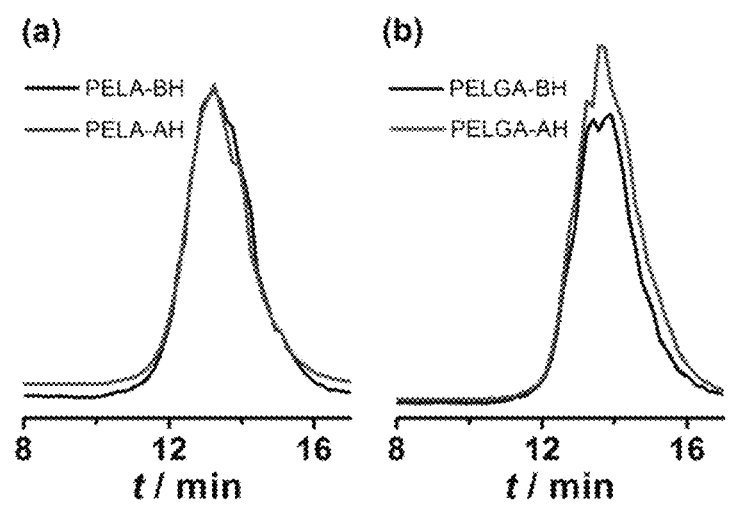
FIG. 13. GPC traces of (a) PELA and (b) PELGA before hydration (BH, black) vs. after hydration (AH, red) in water at rt for 24 h.

Differential Hydration/Dehydration-Induced Modulus, Mass and Volume Changes of PELA and PELGA Films To better understand how hydration and dehydration differentially affect the stiffness of PELA and PELGA films, first quantitated was the tensile moduli of as-prepared, hydrated and dehydrated films. The soft as prepared solvent-cast PELA film, possessing a tensile modulus around 242 MPa at rt, hardened upon immersion in deionized (DI) water, with its elastic tensile modulus reaching ~868 MPa after 24-h hydration at rt (FIG. 8*a*). It should be noted that 24-h hydration did not cause degradation of the polymers as their molecular weights were unchanged upon hydration (FIG. 13). As water evaporated, the PELA film gradually lost its acquired stiffness and eventually reverted to its soft and compliant state (no significant difference in tensile modulus compared to the as prepared film) when fully dehydrated by lyophilization. The tensile modulus of the PELGA film also increased significantly from 142 MPa to 546 MPa when hydrated in DI water at rt. But different from the hydration/dehydration-induced reversible stiffening/softening of PELA, the hydration-induced stiffening of the PELGA film sustained after drying (FIG. 8a).

As expected, the hydrophilic PEG center block improved the water penetration within these amphiphilic polymers, resulting in hydration-induced mass increase by 22% (FIG. 8b) as well as volume increase by 41% and 53% (FIG. 8c) upon 24-h equilibration in DI water for PELA and PELGA, respectively. This swelling ratio translates into ~2.1 and 2.5 water molecules per ethylene glycol repeating unit for PELA and PELGA, respectively. Both PELA and PELGA films shrank back to their initial mass and volume upon drying by lyophilization, supporting that the majority of water absorbed by the amphiphilic polymers were free water rather than structural water.

The reversible mass and volume changes of the PELA film upon hydration/dehydration are consistent with its reversible mechanical stiffening/softening behavior, suggesting that the hydration-modulated mechanics of PELA is driven by reversible structural changes. On the contrary, the reversible mass and volume changes of the PELGA film upon hydration/dehydration did not translate into reversible mechanical stiffening/softening, suggesting that hydration may have induced PELGA to undergo structural changes that are characterized with thermodynamic stability. Such a thermodynamically stable structural change of PELGA may have been sustained upon removal of water, contributing to sustained hydration-acquired stiffness upon drying.

Underlying Structural Changes of PELA and PELGA Films Upon Hydration and Dehydration at Rt To reveal the reversible and thermodynamically stable structural changes of PELA and PELGA as a result of hydration/dehydration, SAXS, DSC and WXRD were carried out. A broad SAXS scattering maximum at ~176 Å (d=$2\pi$/q) was observed with as prepared PELA film (FIG. 9a, top), indicating microphase separation of the incompatible PEG and PLA segments into hydrophobic and hydrophilic domains with an averaged domain separation of ~176 Å. However, the intensity of this scattering was relatively weak, suggesting a relatively small electron density difference between the PLA-rich and PEG-rich domains within the polymer matrix of the as cast film. (Zheng, et al. 2012 *ACS Macro Lett* 1, (5), 641-645; Glatter, et al., *Small Angle X-Ray Scattering*. Academic Press, Orlando, Fla. 1982.) DSC (FIG. 9b, top) and WXRD (FIG. 9c, top) ruled out the formation of sub-nanometer sized crystal structures within the phase-separated domains of the as prepared PELA film, with only a glass transition detected from the DSC scan while no WXRD diffraction peaks observed. Collectively, these results support a weak phase separation within the as prepared cast film of PELA that is characterized with disordered PEG and PLA chain assemblies within the respective hydrophobic and hydrophilic domains.

Figure 9:
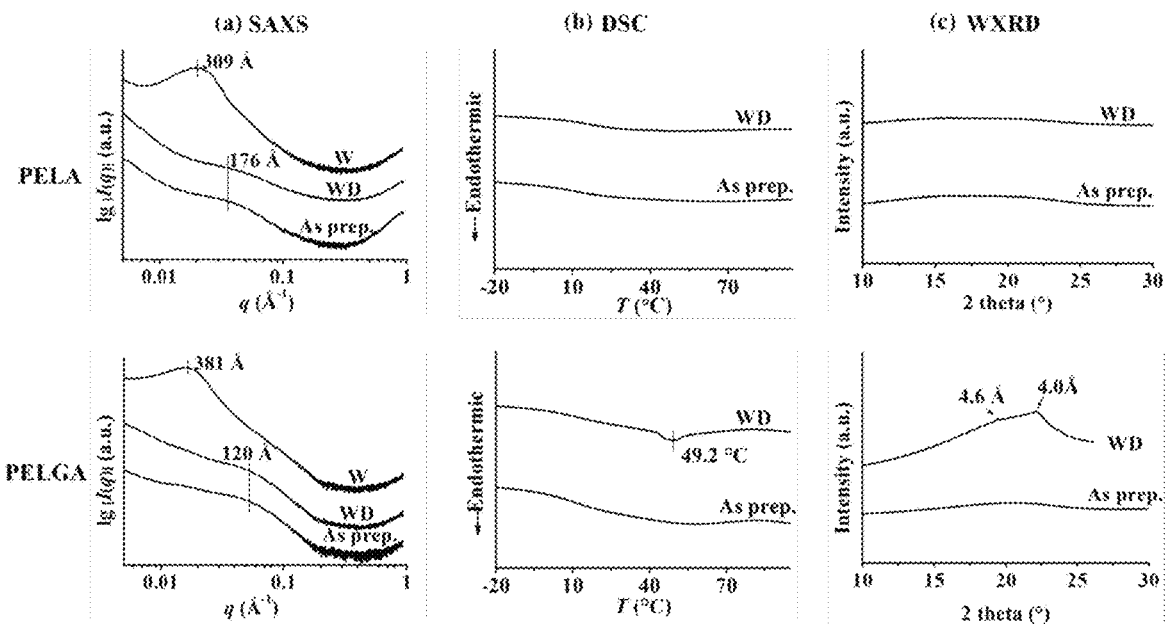
FIG. 9. Structural changes of PELA (top) and PELGA (bottom) in various hydration states at rt as determined by (a) SAXS, (b) DSC (first heating cycle, 10° C./min), and (c) WXRD. As prep.: as prepared cast film; W: wet film after 24-h hydration in DI water; WD: lyophilization-dried film following 24-h hydration in DI water.

Enhanced phase separation was observed upon hydrating PELA at rt as indicated by a stronger and sharper SAXS scattering shifting to a lower q-region centered at 309 Å (FIG. 9a, top, W curve). This larger phase-separated domain separation (309 Å/176 Å, equivalent to 1.8-fold increase) is consistent with the expanded macroscopic volume of PELA films upon hydration, although the degree of macroscopic volume increase appeared smaller (~1.4 fold). When the hydrated PELA film was subsequently lyophilized, its SAXS scattering maximum shifted back to 176 Å along with decreased intensity (FIG. 9a, top WD curve). No obvious difference was observed from the DSC and WXRD profiles before and after hydration (FIGS. 9b & c, top). Overall, the reversible microscopic structural changes of PELA before and after hydration/dehydration revealed by SAXS agreed with the observed reversible macroscopic volume changes and mechanical stiffening/softening. These observations support enhanced microphase separation as an underlying cause for the strengthened mechanical property of PELA film upon hydration at rt.

Figure 14:
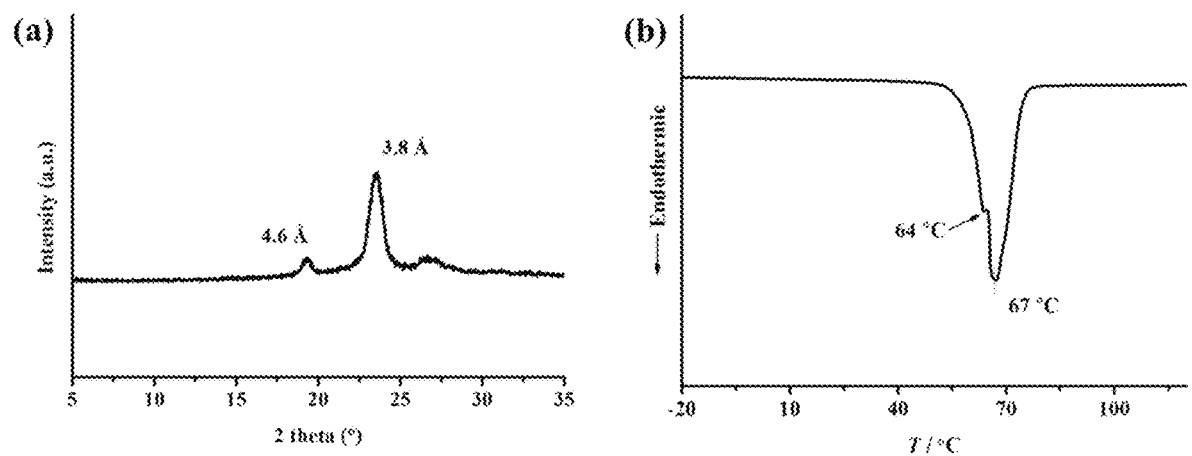
FIG. 14. (a) Wide angle X-ray diffraction of PEG 20k at room temperature and (b) DSC heating trace at a rate of 10° C./min.
Figure 15:
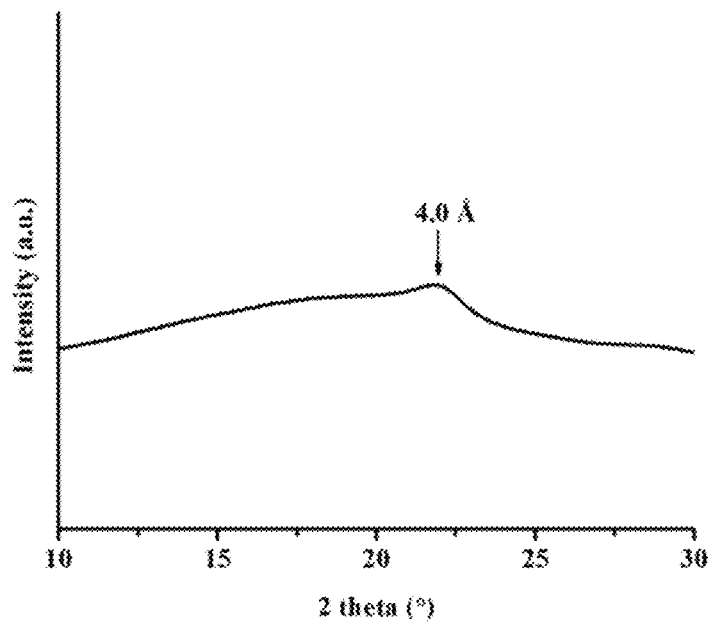
FIG. 15. Wide angle X-ray diffraction of PELGA film in the wet state after hydration at rt for 24 h.
Figure 16:
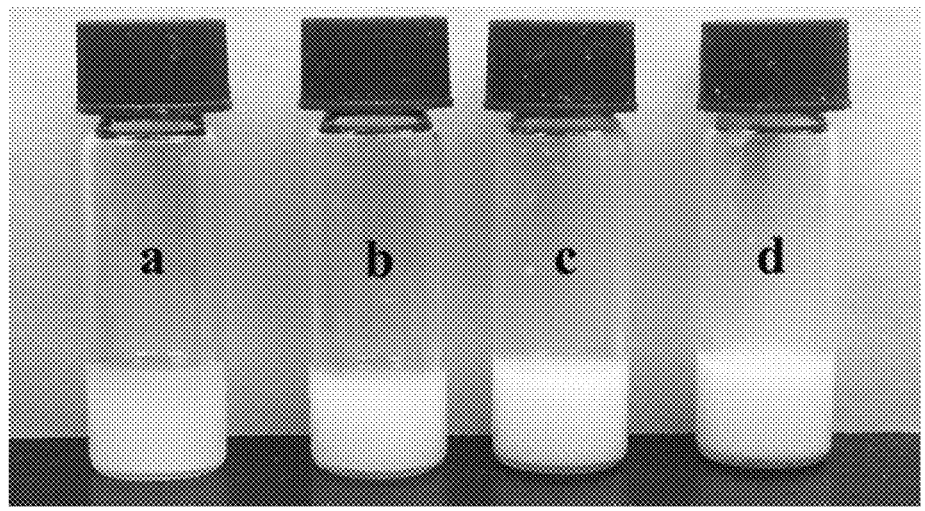
FIG. 16. Stable HA-PELGA(8/1) suspension in dimethylformamide/chloroform(1/4) over 14 h with different HA content. HA/(HA+PELGA): 10 wt % (a); 20 wt % (b); 40 wt % (c); 60 wt % (d).

The PELGA film also underwent reversible microphase separation upon hydration/dehydration as revealed by SAXS, but its domain separations were much different from that observed with PELA. The as prepared cast film of PELGA exhibited a weak SAXS scattering at ~120 Å, which shifted to a lower q-value at 381 Å with enhanced intensity upon rt hydration, and returned to 120 Å after drying (FIG. 9a, bottom). The hydration-induced phase-separated domain expansion ratio for PELGA (381 Å/120 Å=3.2) is much higher than that for PELA (1.8), indicating that PELGA was more readily penetrated by water. This is consistent with the lower steric hindrance imposed by the glycolic acid compared to lactic acid side chain residues which may have translated into higher mobility of the PLGA segments in PELGA. Besides the reversible microphase separation, however, PELGA also exhibited distinctive structural changes in the sub-nanometer regime after hydration that was not observed in PELA as revealed by DSC and WXRD. DSC detected a broad endothermic process ~40-70° C. during heating of the as prepared cast film of PELGA (FIG. 9b, bottom, curve "As prep."), which may be attributable to the chain rearrangement of PEG segments. No detectable crystalline signal was observed from WXRD of the as prepared PELGA cast film (FIG. 9c, bottom, curve "As prep"). By contrast, a more pronounced endothermic peak at ~49° C. was observed by DSC scan of the PELGA cast film after hydration, implying a melt process of crystalized PEG. This speculation was supported by WXRD wherein two peaks at 4.6 and 4.0 Å were observed with hydrated but subsequently lyophilized PELGA film (FIG. 9c, bottom, curve WD). These diffractions are consistent with those of the crystalline PEG20k (FIG. 14a) and reported PEG segments in PELGA block copolymers, and unlikely associated with poly(D,L-lactide-co-glycolide) segments which tend to be amorphous. (Chen, et al. 2014 *RSC Adv.* 4, (17), 8789-8798; Saliba, et al. 2012 *Quim. Nova* 35, (4), 723-727; Ignjatovic, et al. 20071 *Eur. Ceram. Soc.* 27, (2-3), 1589-1594.) Meanwhile, the wet PELGA film also gave a diffuse diffraction peak at ~4.0 Å (FIG. 15). This hydration-facilitated PEG crystallization, in addition to microphase seperation, has likely contributed to the observed hydration-induced mechanical strengthening of the PELGA film. It should be noted that the melting transition of PEG segments in PELGA, however, is >10° C. lower than that of pure PEG20k (FIG. 14b). This phenomenon is often observed in imperfect crystals containing defects/impurities with reduced thermodynamic stability. (d'Acunzo, et al. 2002 *Macromolecules* 35, (25), 9360-9365.) Thus, rt hydration likely promoted imperfect crystallization of the PEG chains in PELGA.

Models for Hydration-Induced Stiffening of PELA and PELGA

Figure 10:
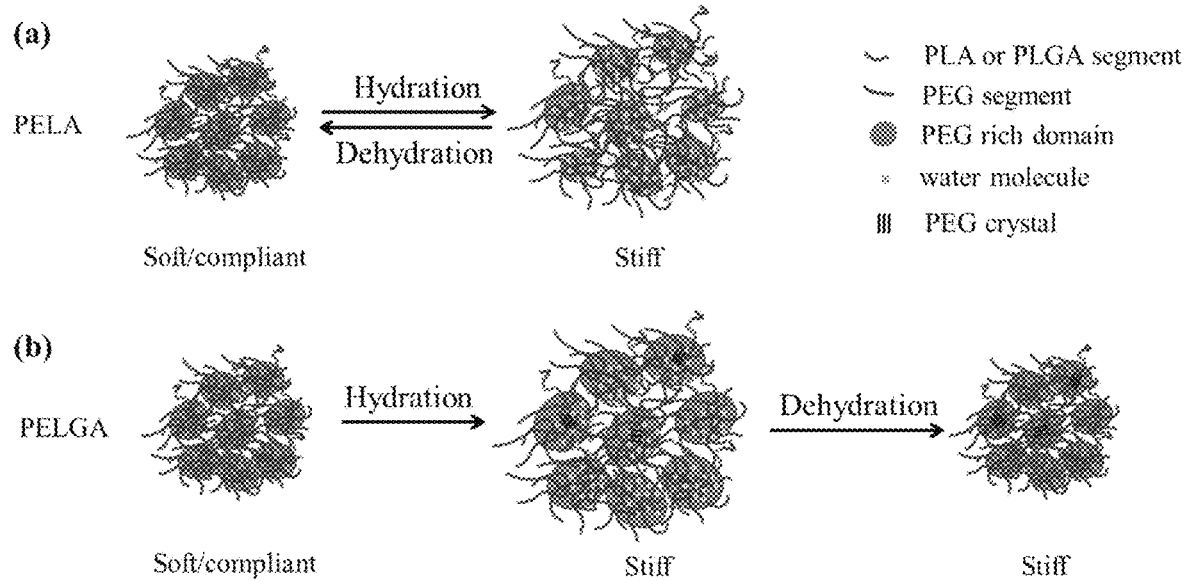
FIG. 10. Proposed models for differential structural and mechanical property changes of PELA and PELGA upon rt hydration and dehydration. (a) A model of reversible phase separation upon rt hydration and dehydration of PELA. (b) A model of reversible phase separation and irreversible PEG crystallization upon rt hydration and dehydration of PELGA.

Small molecules including water often act as plasticizers to soften materials when blended into polymer. Here it was shown that in amphiphilic block copolymers PELA and PELGA, water induced micro-structural changes that translated into strengthened mechanical properties instead. As depicted in FIG. 10, the polymer chains in as prepared PELA and PELGA cast films adopt a "relaxed" amorphous conformation in the soft and compliant state of these materials. When water molecules penetrate through the hydrophobic segments and stabilized within PEG-rich domains, the polymer network undergoes enhanced microphase separation and is forced to expand, resulting in an increased volume and enhanced rigidity of the material. It was reported that swollen PEG-rich domains in crosslinked polymer networks could impose mechanical stress to the surrounding hydrophobic matrix, resulting in improved mechanical integrity of the material. (Xu, et al. 2007 *J. Am. Chem. Soc.* 129, (3), 506-507.) Similar observation was also reported in random copolymers containing hydrophobic blocks and PEG segments. (Bedoui, et al. 2012 *Soft Matter* 8, (7), 2230-2236.) It is believed that besides the swelling pressure imposed by water molecules within the PEG-rich domains, the extension of polymer chains from their original "relaxed" state to a more taut state may have also contributed to the stiffening of the material. In the case of the PELA film, upon removal of water, the taut polymer chains shrunk back to their more relaxed state to release the internal stress, resulting in the softening of the material. Unlike PELA, PEG crystallization accompanies the microphase separation within PELGA upon rt hydration, and the more stably formed PEG crystallites within the polymer network are responsible for its sustained stiffening even upon lyophilization. Meanwhile, the more mobile hydrophobic PLGA segments in PELGA (compared to PLA segments in PELA) likely play an essential role in ensuring effective microphase separation upon rt hydration and permitting an sufficient yet not excessive amount of water to be localized in PEG-rich domains to facilitate the crystallization rather than dissolution of the hydrophilic PEG chains as reported. (Bedoui, et al. 2012 *Soft Matter* 8, (7), 2230-2236.) Although PEG is generally considered water soluble, in case of hydrated PELGA, the PEG segments adopt a higher local concentration within the swelled PEG rich domain (~0.96 g PEG in 1 mL water). Comparing to the low solubility of 50 mg/mL of PEG20k in water at 25° C., such a supra-saturated local concentration of PEG would likely lead to some degree of PEG crystallization.

Figure 11:
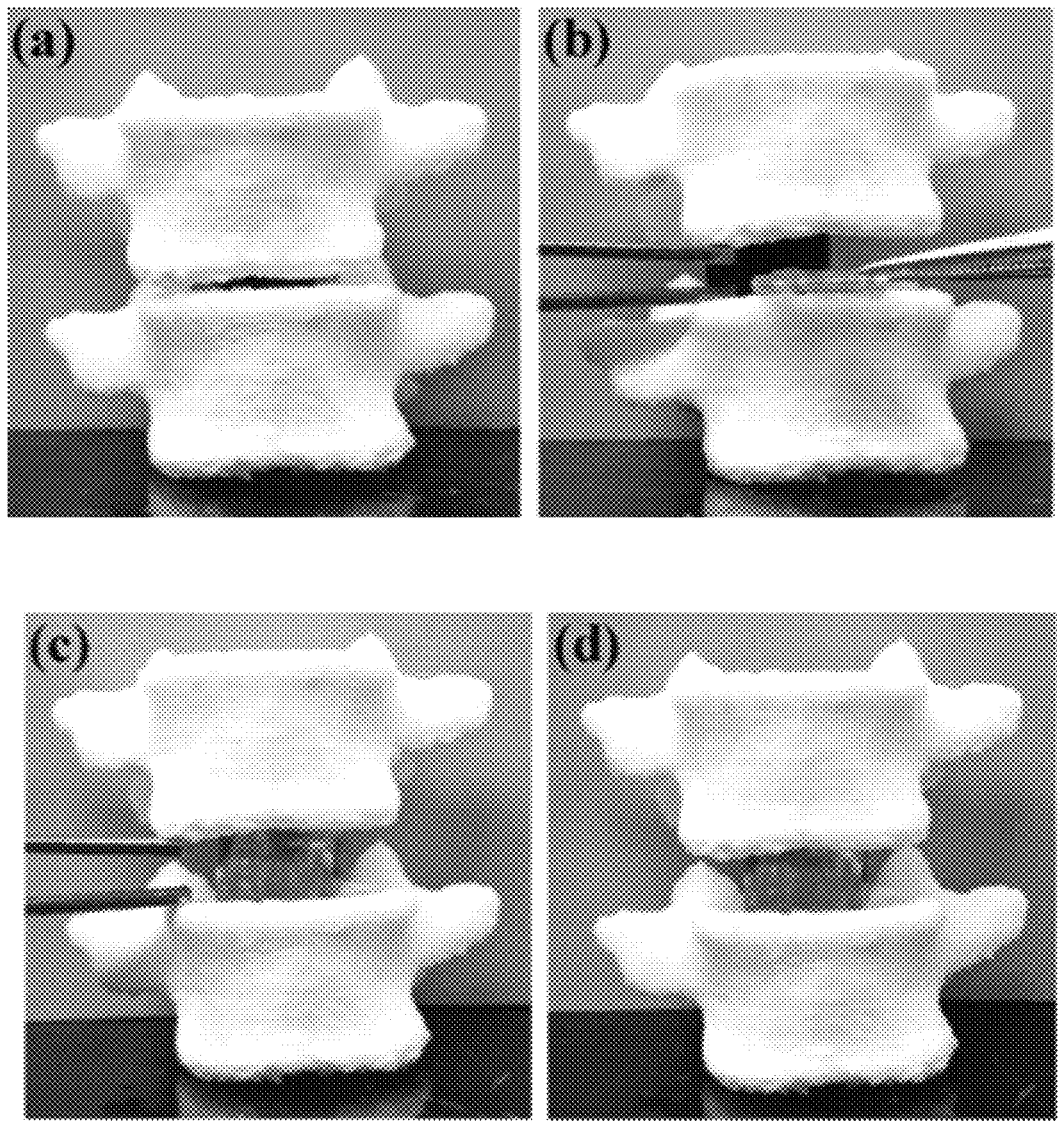
FIG. 11. Demonstration of potential application of the amphiphilic SMP for restoring collpased disc space. (a) 3-D printed vertebral segments showing a collapsed disc space; (b) Insertion of a compressed PELGA disc (temporary shape) into the to be restored disc sapce; (c) Shape recovery of the PELGA disc triggered by warm saline rinse to fill the disc space; (d) Stiffened hydrated PELGA within the restored disc space. The PELGA disc was marked by red sharpie for easy visualization.

The unique hydration-induced stiffening of PELA and PELGA, combined with their facile shape recovery in warm water, may open possibilities of applying these SMPs for weight-bearing biological applications. For instance, they may be applied as resorbable spine fusion cages or artificial discs for restoring collapsed vertebral disc space (FIG. 11) where their delivery in a minimally invasive temporary configuration, facile shape recovery to fill the defect, and subsequent stiffening upon wetting all present unique translational advantageous.

In summary, disclosed herein for the first time a facile shape recovery of amphiphilic triblock SMPs PELA and PELGA in warm water with concomitant strengthening of mechanical properties, and elucidated that microphase separation and PEG crystallization are responsible for their unusual hydration-induced stiffening behavior. Whereas the hardening of PELA in water at rt was primarily driven by microphase separation, hydration-acquired rigidity in PELGA film at rt resulted from both microphase separation and PEG crystallization. It was also demonstrated that by adjusting the chemical composition of the degradable blocks (PLA vs. PLGA blocks), one can practically regulate their mechanical properties for applications where hydration-induced stiffening needs to be maintained upon subsequent dehydration. It should be noted that an appropriate balance of hydrophobic vs. hydrophilic block content is likely required to ensure that PEG crystallization rather than dissolution preferentially occurs upon hydration. This study illustrates a new strategy for the rational design of SMPs capable of strengthening their mechanical strengths upon shape recovery in an aqueous environment, broadening their utilities for weight-bearing biological applications under physiological conditions.

Figure 17:
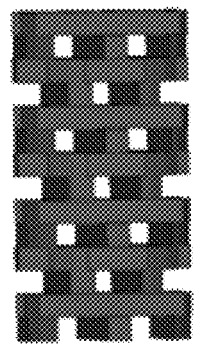
FIG. 17. Smart-fitting of a 3D macroporous HA-PELGA implant in 5-mm rat femoral segmental defect. (A) CAD of macroporous graft; (B) Insertion of graft in compressed temporary shape and warm saline rinse triggering its shape recovery, swelling and stiffening within the defect.
Figure 17:
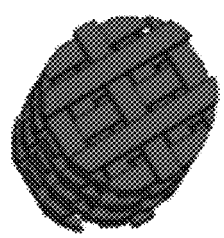
Figure 17:
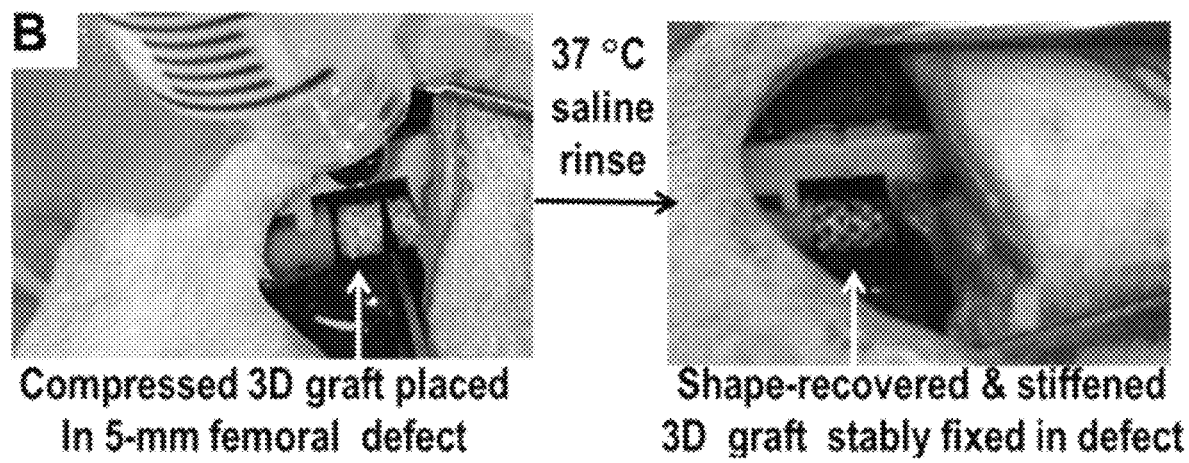
Figure 18:
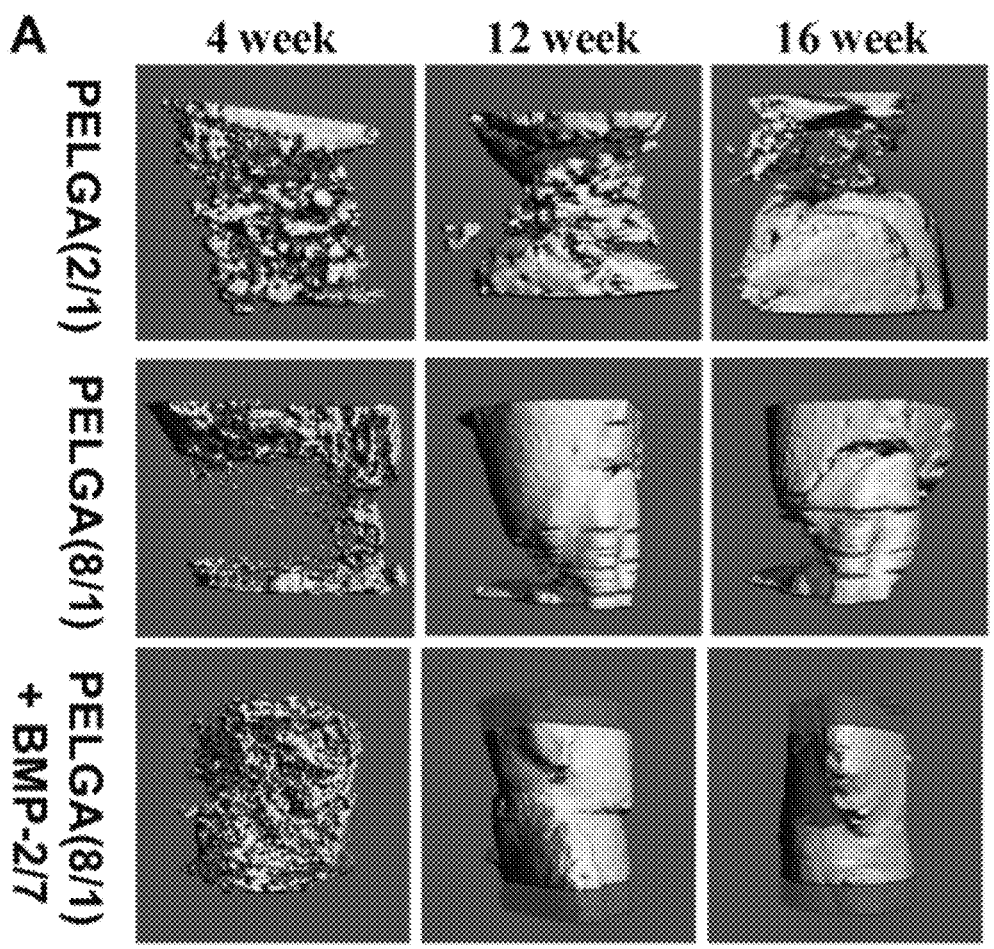
FIG. 18. 3D HA-PELGA (2/1 or 8/1; 25% HA), with/without 400-ng rhBMP-2/7 guided bone regeneration within 5-mm rat femoral segmental defect. (A) microCT images of regenerated bone at the defect site over time (thresholded to exclude scaffold background). Scale bar: 300 um. (B) Histology of the center of regenerated bone tissue guided by scaffold at 12 and 16 weeks post-op. (C) Maximal torque of 16-week regenerated bone tissue guided by the HA-PELGA (8/1)+BMP group vs. health controls (p>0.05; no significant difference).
Figure 18:
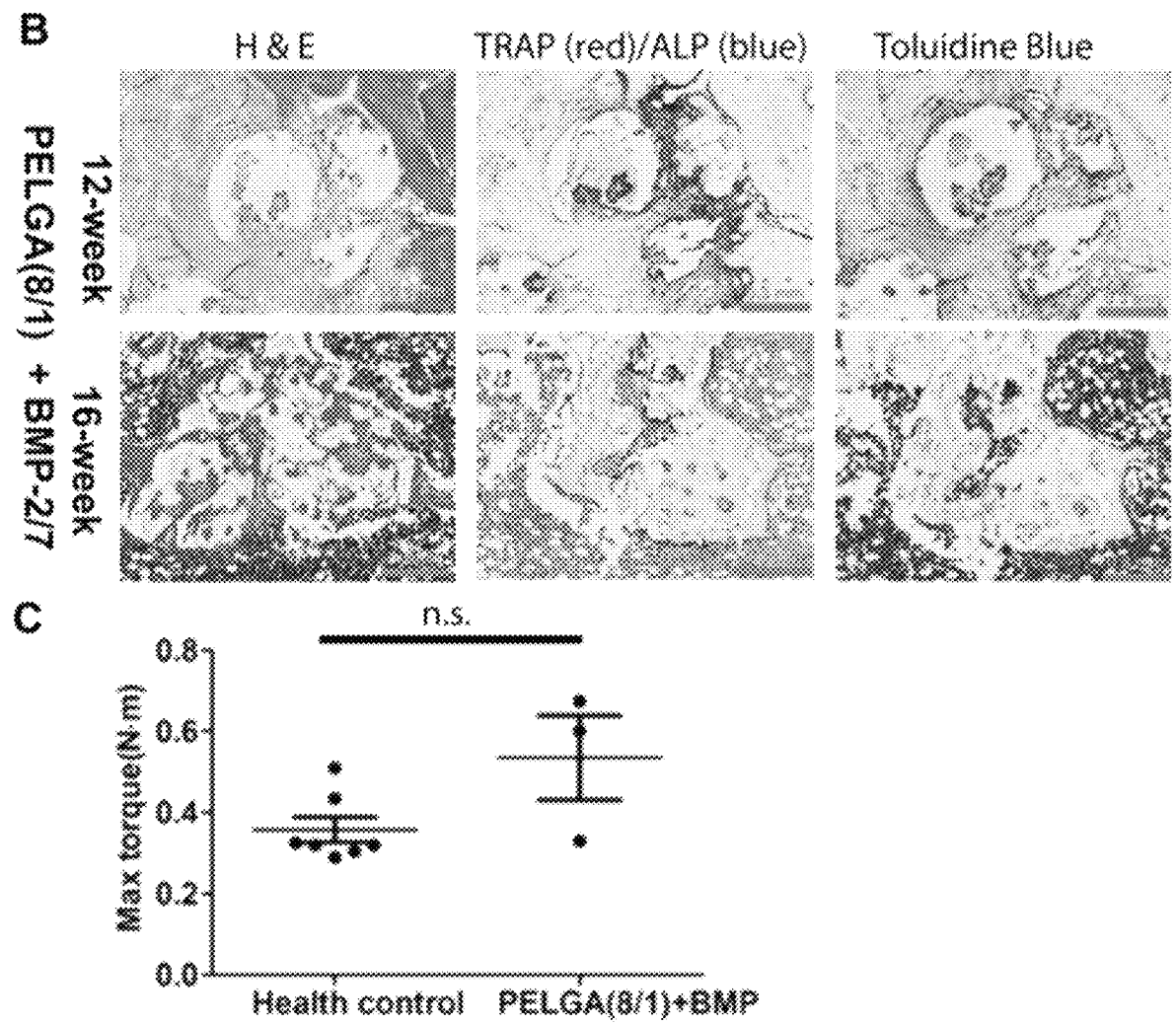

3-D printed macroporous HA-PELGA grafts of various compositions (e.g., LA/GA 8:1 to 2:1; HA content 10-25%) and macroporositities (e.g., 65% overall porosity) were smart-fixed within critical-size 5-mm rat femoral segmental defect (FIG. 17) and successfully guide the regeneration of bone without or with a single low dose of osteogenic bone morphogenetic protein (BMP) therapeutics as supported by microCT, histology and torsion analyses (FIG. 18). In the absence of rhBMP-2/7, both graft compositions templated robust bone formation over time, while with 400-ng rhBMP-2/7, bone formation was further expedited. In the presence of BMP-2/7, by 12 weeks, the macropores of the scaffold has been filled with new, maturing/remodeling bone as supported by histology (red TRAP stain and blue ALP stain indicate coordinated osteoclastic and osteoblastic remodeling while purple toluidine blue stain indicates residue cartilageous matrix undergoing endochondral ossification); while by 16 weeks, synthetic scaffolds were completely degraded and replaced with matured new bone that has been successfully recanalized (fill with bone marrow). Torsional strength of regenerated bone showed no statistically significant difference compared to healthy controls, supporting full functional restoration of torsional strength of the defect.

Experimental Section

Materials

D,L-lactide and glycolide were purchased from Sigma-Aldrich (St. Louis, Mo.) and purified by recrystallization twice in anhydrous toluene and dried under vacuum prior to use. PEG (BioUltra, 20,000 Dalton) was purchased from Fluka (Switzerland). Polycrystalline HA powder was purchased from Alfa Aesar (Ward Hill, Mass.). All other solvents and reagents were purchased from Sigma-Aldrich (St. Louis, Mo.) and used as received.

Synthesis of PELHA(8/1)

PEG (20,000 Dalton, 1.0 g, 0.050 mmol) was heated to 100° C. in a Schlenk flask and stirred under vacuum for 2 h to remove residual water. The melt was cooled to r.t. before Sn(II) 2-ethylhexanoate (95%, 3 mg, 0.0074 mmol) in 30 μL anhydrous toluene was added. After heating the mixture under vacuum at 100° C. for 15 min to remove toluene, D,L-lactide (4.7 g, 33 mmol) and glycolide (0.41 g, 3.5 mmol) were added when the system was cooled to r.t, and then temperature was elevated to proceed polymerization at 130° C. for 4 h under argon with stirring. The crude polymer PELGA (8/1) was dissolved in chloroform and purified by precipitation in methanol/ether mixture (7/1, v/v) to afford 5.1 g (83%) colorless product after drying in vacuum. $^1$H NMR (CDCl$_3$, 400 MHz): 5.17 (m, 1160H), 4.82 (m, 292H), 3.64 (m, 1818H), 1.56 (m, 4537H) ppm. The actual incorporation ratio of lactide to glycolide of 8/1 was calculated from the integration intensity (I) of proton signals at ~5.17 ppm (PLA) vs. ~4.82 ppm (PGA) per equation: I(5.17 ppm)/(I(4.82 ppm)/2).

Synthesis of PELGA(2/1)

The synthetic procedure is the same as that of PELGA (8/1) except that lactide/glycolide feed amount was 3.7 g and 1.3 g, respectively, affording colorless product at 83% yield. $^1$H NMR (CDCl$_3$, 400 MHz): δ 5.16 (m, 833H), 4.80 (m, 861H), 3.64 (m, 1818H), 1.57 (m, 3553H) ppm. The actual incorporation ratio of lactide to glycolide of 2/1 was calculated from the integration intensity (I) of proton signals at ~5.16 ppm (PLA) vs. ~4.80 ppm (PGA) per equation: I(5.16 ppm)/(I(4.80 ppm)/2).

Electrospining of PELGA and HA-PELGA Scaffolds

PELGAs composite scaffolds with 0 and 10 wt % HA were prepared by electrospinning. Polycrystalline HA powder (0.14 g) was bath-sonicated in 5 ml 1:4 (v/v) dimethylformamide/chloroform for 30 min to break up aggregates before PELGA (1.25 g) was added. The mixture was stirred overnight at r.t. and loaded into a 5 ml syringe. A high-voltage power supply (Gamma High Voltage Research, Ormond Beach, Fla.) was set to delivered a voltage of 12 kV between a 22 G ejection needle and an aluminum collection plate set 15 cm away. The polymer solution was fed through the needle at rate of 0.7 ml h$^{-1}$ with a syringe pump (Orion Sage M361, Thermo Scientific, Billerica, Mass.), and the fibers were collected on the aluminum collector plate. The electrospinning proceeded for 3 h, with the collecting plate rotated by 90° every 15 min to ensure homogeneity of the fibrous scaffold. The collected scaffolds were dried in a vacuum oven at r.t. to remove any residual solvent and stored in a desiccator at 4° C. All meshes were sterilized under ultraviolet light for 2 h, then equilibrated in media prior to cell culture use.

Stress-Controlled Cyclic Thermal Mechanical Testing

As-spun HA-PELGA specimens (5.3 mm×35 mm×≈0.15 mm) were equilibrated at 50° C. for 10 min to erase any thermal history and cooled to 25° C. prior to testing. After being equilibrated at 25° C. for 5 min, the specimens were subjected to a 0.3 MPa (for HA-PELGA(8/1)) or 0.2 MPa (for HA-PELGA(2/1)) tensile stress, and cooled at 2° C. min$^{-1}$ to 0° C., while the respective constant stress was maintained. This yielded the elongated temporary shape under stress $\varepsilon_1$. After being held at 0° C. for 5 min, the stress was released to a 1 mN preload force. The resulting strain was recorded as the unloaded temporary shape $\varepsilon_u$. Shape recovery was triggered by heating the specimens at a rate of 2° C. min$^{-1}$ to 50° C. and holding at 50° C. for 10 min. The recovered sample strain was recorded as $\varepsilon_p$. Each specimen was subjected to three consecutive cycles of testing. The $R_f$ and $R_r$ were determined based on the second cycle using Equation (1) and (2).

$$R_f(N) = \frac{\varepsilon_u(N) - \varepsilon_p(N-1)}{\varepsilon_1(N) - \varepsilon_p(N-1)} \quad (1)$$

$$R_r(N) = \frac{\varepsilon_u(N) - \varepsilon_p(N)}{\varepsilon_u(N) - \varepsilon_p(N-1)} \quad (2)$$

Cell Seeding, Proliferation and Osteogenic Differentiation of Rat PDCs on HA-PELGA Electrospun Meshes Rat PDCs were isolated from femurs and tibiae of 4-week-old male Charles River SASCO SD rats by enzymatic digestion in αMEM (without ascorbic acid) solution of 2.5-mg/mL type 2 collagenase (Worthington, Lakewood, N.J.) as previously described. (Filion, et al. 20131 Biomater. Tissue Eng. 3, 486.) Cells were pelleted, resuspended and expanded in αMEM without ascorbic acid supplemented with 20% FBS (Hyclone) and 2% L-glutamine, and 1% penicillin-streptomycin (expansion media). Passage 1 PDCs were seeded on sterile HA-PELGA(2/1) or HA-PELGA(8/1) meshes (n=5), sized to fit in 96-well tissue culture plates, in 20-μL expansion media to achieve an initial seeding density of 1.0×10$^5$ cells/cm$^2$. Additional 20-μL media was supplemented in batches within the next 5 h to provide enough nutrients and enable the cells adhere to the mesh in ultralow adhesion plate before another 110-μL expansion media were added to each well. Media were changed every other day, and the viability of cells adhered on the meshes over time was determined using the CCK-8 (Dojindo, Japan) kit per vendor instructions. The absorbance was read at 450 nm on a Multiskan FC Microplate Photometer (Thermo Scientific, Billerica, Mass.). The meshes were also fixed and stained on day 5 with MTT.

For osteogenic differentiation, passage 1 PDCs were seeded on the respective HA-PELGA meshes in the manner described above to achieve an initial seeding density of 2.5×10$^5$ cells/cm$^2$. After culturing the cells adhered to the mesh in expansion media in 96-well ultralow adhesion plates for 3 days, the media were replaced with osteogenic media (expansion media supplemented with 10 nM dexamethasone, 20 μM β-glycerol phosphate, and 50 μM 1-ascorbic acid 2-phosphate). Cells were cultured for 11 days in osteogenic media with media changes 3 times a week before they were stained by alkaline phosphatase (ALP).

Transfection, Culture, and Cell Sheet Release and Transferring of GFP-BMSCs to HA-PELGA Electrospun Meshes BMSCs were isolated from the marrow cavity of tibia and femurs of 4 week old male Charles River SASCO SD rats and enriched by adherent culture in expansion media as previous described. (Song, et al. 2009 J. Biomed. Mater. Res., Part A, 89A, 1098.) Passage 1 BMSCs were transduced with lentiviral vectors (Cellomics Technology, Halethorpe, Md.) expressing enhanced GFP driven by elongation factor-1 alpha (EF1α), and retained osteogenesis and adipogenesis of GFP-BMSCs were validated as previously reported. (Kutikov, et al. 2015 ACS Applied Materials & Interfaces 7, 4890.) Passage 3 GFP-BMSCs were seeded on Nunc UpCell™ culture dish (Thermo Scientific) and cultured in expansion media at 37° C. until reaching confluency. Upon removing culture media, an HA-PELGA(2/1) electrospun mesh was placed over the cell layer before the culture dish was placed at 4° C. for 30 s to allow the confluent cell sheet to detach and transferred to the mesh. Meshes with and without the transferred cell sheets of GFP-BMSC were imaged by fluorescent microscopy (Zeiss Axiovert 40 CFL).

Syntheses and Characterizations of PELGA and PELA

In a typical synthesis of PELGA, PEG (20,000 Dalton, 1.0 g, 0.050 mmol) was heated to 100° C. in a Schlenk flask and stirred under vacuum for 2 h to remove residual water. The melt was cooled to room temperature before Sn(II) 2-ethylhexanoate (95%, 3 mg, 0.0074 mmol) in 30 μL anhydrous toluene was added. After heating the mixture under vacuum at 100° C. for 15 min to remove toluene, the mixture was cooled to rt for the addition of D,L-lactide (2.8 g, 33 mmol) and glycolide (2.2 g, 3.5 mmol) before the temperature was elevated to 130° C. to allow the polymerization to proceed for 5 h under argon with stirring. The crude polymer PELGA was dissolved in chloroform and purified by precipitation in methanol/ether mixture (7/1, v/v) to afford 5.0 g (84%) colorless product ($M_w$=80119, PDI=1.7) after drying in vacuum. PELA ($M_w$=94761; PDI=1.7) was synthesized following prior report. (Kutikov, et al. 2013 Acta Biomater. 9, (9), 8354-8364.)

The molecular weights and polydispersity of PELA and PELGA were determined by gel-permeation chromatography (GPC) on a Varian Prostar HPLC system equipped with two 5 mm PLGel MiniMIX-D columns (Agilent, Santa Clara, Calif.) and a PL-ELS2100 evaporative light scattering detector (Polymer Laboratories, UK). THF was used as an eluent at 0.3 ml/h at rt. Molecular weight and polydispersity calculations were calibrated with EasiVial polystyrene standards (Agilent, Santa Clara, Calif.). The actual glycolide to lactide incorporation ratio in PELGA was determined by $^1$H NMR integration (FIG. 12).

Table 1 shows molecular weights of PELGA polymers with different lactic to glycolic acid ratios.

TABLE 1

| | Molecular Weight and PDI | | | |
|---|---|---|---|---|
| lactic/ glycolic ratio | 19/1 | 8/1 | 2/1 | 4/5 |
| $M_w$ | ~100000 | ~70000-120000 | 70000-110000 | 70000-140000 |
| PDI | ~1.7 | ~1.7 | ~1.7 | ~1.7 |

Preparation of Dense PELGA and PELA Films

Solvent cast films of PELGA or PELA were prepared by dissolving ~1 g PELGA or PELA in ~3 mL of chloroform and poured into a Teflon mold, which was left in a ventilated fumehood overnight to allow most chloroform to evaporate. The cast film was further dried under vacuum at rt.

$^1$H NMR Spectra $^1$H NMR spectra were recorded on a Varian Mercury 400 MHz spectrometer at 298 K using CDCl$_3$ as the solvent and chemical shifts were quoted to internal standard tetramethylsilane.

Molecular Weight Determination by GPC

The molecular weights and polydispersity of PELGAs were determined by GPC on a Varian Prostar HPLC system equipped with two 5 mm PLGel MiniMIX-D columns (Agilent, Santa Clara, Calif.) and a PL-ELS2100 evaporative light scattering detector (Polymer Laboratories, UK). Tetrahydrofuran (THF) was used as an eluent at 0.3 ml·h$^{-1}$ at r.t. Molecular weight and polydispersity calculations were calibrated with EasiVial polystyrene standards (Agilent, Santa Clara, Calif.).

SEM Characterization of Electrospun Meshes

Scaffolds were sputter coated with Au (~4 nm thick) and imaged on a Quanta 200 FEG MKII scanning electron microscope (FEI Inc., Hillsboro, Oreg.) under high vacuum at 5 kV. Fiber diameters were determined from the SEM micrographs by analyzing 100 fibers randomly chosen in five different fields of view using ImageJ (National Institutes of Health).

Cyclic Thermal Mechanical Charaterization of Shape Memroy Properties

Cyclic thermal mechanical testing was carried out on a DMA Q800 equipped with a gas-cooling accessory. Specimens (5.3 mm×15 mm×≈0.15 mm) were equilibrated at 55° C. for 5 min and cooled to 25° C. prior to testing. After being equilibrated at 25° C. for 5 min, the specimens were subjected to a 0.15 MPa tensile stress, and cooled at 2° C. min$^{-1}$ to 4° C., while the constant stress was maintained. This yielded the elongated temporary shape under stress $\varepsilon_l$. After being held at 4° C. for 5 min, the force was released to a 1 mN force. The resulting strain was recorded as the unloaded temporary shape $\varepsilon_u$. Shape recovery was triggered by heating the specimens at a rate of 2° C. min$^{-1}$ to 55° C. and holding at 55° C. for 5 min. The recovered sample strain was recorded as $\varepsilon_p$. Each specimen was subjected to three consecutive cycles of testing. The shape fixing ratio ($R_f$) and shape recovery ratio ($R_r$) were calculated from the second cycle per Equations 1 and 2 where N is 2:

$$R_f(N) = \frac{\varepsilon_u(N) - \varepsilon_p(N-1)}{\varepsilon_l(N) - \varepsilon_p(N-1)} \quad (1)$$

$$R_r(N) = \frac{\varepsilon_u(N) - \varepsilon_p(N)}{\varepsilon_u(N) - \varepsilon_p(N-1)} \quad (2)$$

Tensile Mechanical Test

The tensile modulus of electrospun PELGA and HA-EPLGA scaffolds at r.t. were determined on a MTS Bionix 370 mechanical testing system (MTS Systems Corporation, Minneapolis, Minn., USA) based on ASTM D882-97 guidelines. As-spun or hydrated but subsequently lyophilized specimens (5 mm×40 mm×~0.2 mm, n=5) were loaded onto the MTS machine with an initial grip separation of ~10 mm and subjected to a grip separation at a rate of 100 mm min$^{-1}$. The resulting force was recorded with a 250 N load cell (Interface, Scottsdale, Ariz.). Tensile modulus was calculated as slope of a secant line between 0.05% and 0.25% strain on a stress-strain plot according to standard ISO 527. The initial toe region, if present, was excluded from the modulus calculation.

The tensile modulus of PELA and PELGA films (5 mm×40 mm×~0.15 mm) at rt were determined on a MTS Bionix 370 mechanical testing system (MTS Systems Corporation, Minneapolis, Minn., USA) based on ASTM D882-97 guidelines. Specimens (n=5) were loaded onto the MTS machine with an initial grip separation of ~10 mm and subjected to a grip separation rate of 100 mm·min$^{-1}$. The force was recorded with a 250-N load cell (Interface, Scottsdale, Ariz.). Tensile modulus is calculated as slope of the linear region (between 0.05% and 0.25% strain) of the recorded stress-strain curve according to standard ISO 527.

Differential Scanning Calorimetry (DSC)

DSC experiments were conducted on a Q200 MDSC (TA Instruments, New Castle, Del.) at a heating rate of 10° C./min with a sample load of ~1.5 mg in an aluminum pan with the pan weight identically matched to the reference pan.

XRD Experiments

XRD experiments were performed on a Bruker D8 Discover diffractometer with GADDS as a 2D detector or a Philips X'Pert Pro diffractometer with a 1.8 kW ceramic tube as the X-ray source (Cu Kα) and an X'celerator detector, calibrated by silicon powder (2θ>15°) and silver behenate (2θ<15°). Data were collected between 2θ range of 5° to 35°.

Wide-Angle X-Ray Diffraction (WXRD)

WXRD experiments were performed on a Rigaku Xta-LAB MM007-HF including a MicroMax-007 HF Microfocus rotating anode X-ray generator, Osmic optics and a Saturn HG CCD detector. The obtained diffraction patterns are converted to 1D profile by Saxsgui software.

Small-Angle X-Ray Scattering (SAXS)

SAXS measurements were performed at 12-ID-B at the Advanced Photon Source at Argonne National Laboratory. Monochromatic X-rays (X-ray energy is 14 keV and wavelength is 0.8856 Å) were focused on samples with a size of 0.3×0.02 mm$^2$ (H×S) and the scattered signals were collected on a Pilatus 2M detector for small angle and Pilatus 300K detector for wide angle. The small angle and wide angle detectors were located about 2 and 0.3 meters downstream of a sample, respectively. The scattering angle 2θ was calibrated with silver behenate standard and converted into scattering vector q scale, where q=4π sin θ/λ. The scattered intensity was corrected for transmittance and instrument background.

In vivo implantation of 3-D printed macroporous HA-PELGA scaffold to guide the regeneration of 5-mm rat femoral segmental defect. HA-PELGA(8/1) or HA-PELGA (2/1) with 10-25% HA were extruded into filaments and fed onto 3-D printer to prepare 3-D macroporous scaffolds. 5-5.4 mm tall and ~3-mm in diameter cylinders are cored out as synthetic grafts to augment the repair of 5-mm femoral segmental defect in skeletally mature rats, with and without the absorption of a single dose of 400-ng osteogenic growth factor rhBMP-27 heterodimer. The synthetic graft was compressed into a shorter cylinder at rt for convenient placement within the defect, and warm saline rinse (37° C.) then triggered its shape recovery/swelling and stiffening within the defect to achieve 100% long-term fixation success through the course of 16 week follow-up as supported by longitudinal microCT monitoring and end-point histology (H&E, alkaline phosphatase/ALP and tartrate-resistant alkaline phosphate/TRAP, toluidine blue staining) and torsion test.

Applicant's disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the descriptions, herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

The invention claimed is:

1. A self-fitting implant or device, comprising an amphiphilic and biodegradable thermoplastic co-polymer comprising blocks of poly(ethylene glycol) and blocks of poly (lactic-co-glycolic acid) forming a 2-D or 3-D scaffold, wherein the molar ratio of lactic acid to glycolic acid is about 19 to about 0.8.

2. The self-fitting implant or device of claim 1, wherein the molar ratio of ethylene glycol to (lactic acid and glycolic acid) is about 0.27 to about 0.79.

3. The self-fitting implant or device of claim 2, wherein the amphiphilic and biodegradable thermoplastic co-polymer is characterized by a molecular weight $M_w$ from about 70,000 to about 140,000 with the molecular weight of blocks of poly(ethylene glycol) ranging from about 19,000 to about 21,000 and the molecular weight $M_w$ of blocks of poly (lactic-co-glycolic acid) ranging from about 50,000 to about 120,000.

4. The self-fitting implant or device of claim 3, wherein the molar ratio of lactic acid to glycolic acid is about 10 to about 0.8.

5. The self-fitting implant or device of claim 4, wherein the molar ratio of ethylene glycol to (lactic acid+glycolic acid) is about 0.58 to about 0.79.

6. The self-fitting implant or device of claim 5, characterized by an enhanced mechanical strength upon hydration.

7. The self-fitting implant or device of claim 6, wherein the mechanical strength upon hydration is enhanced by microphase separation and/or crystallization.

8. The self-fitting implant or device of claim 3, wherein the thermoplastic co-polymer forms a 3-D scaffold.

9. The self-fitting implant or device of claim 8, further comprising one or more inorganic minerals attached to or encapsulated in the 3-D scaffold.

10. The self-fitting implant or device of claim 9, wherein the one or more inorganic minerals are selected from the group consisting of calcium apatites, calcium phosphates, hydroxyapatite, and substituted hydroxyapatites.

11. The self-fitting implant or device of claim 10, having a shape of a mesh, sheet, wire, rod, plate, cylinder or a shape matching with that of a tissue defect.

12. The self-fitting implant or device of claim 11, having a longest dimension in the range from about 1 mm to about 20 cm and a shortest dimension in the range from about 0.2 mm to about 5 cm.

13. The self-fitting implant or device of claim 11, further comprising a bioactive material selected from the group consisting of cells, growth factors, cytokines, gene vectors, antibiotics, drugs, and bacterial phage.

14. The self-fitting implant or device of claim 11, wherein the molar ratio of lactic acid to glycolic acid is about 19 to about 0.8 and the molar ratio of ethylene glycol to (lactic acid+glycolic acid) is about 0.58 to about 0.79.

* * * * *